United States Patent [19]

Goering et al.

[11] 4,428,967

[45] * Jan. 31, 1984

[54] PROCESSES FOR PRODUCTION OF WAXY BARLEY PRODUCTS

[75] Inventors: Kenneth J. Goering; Robert F. Eslick, both of Bozeman, Mont.

[73] Assignee: Research and Development Institute, Inc., at Montana State University, Bozeman, Mont.

[*] Notice: The portion of the term of this patent subsequent to Jan. 19, 1999 has been disclaimed.

[21] Appl. No.: 313,242

[22] Filed: Oct. 20, 1981

Related U.S. Application Data

[63] Continuation-in-part of Ser. No. 47,855, Jun. 12, 1979, Pat. No. 4,311,714.

[51] Int. Cl.³ ............................ A23L 1/09; A23J 1/12
[52] U.S. Cl. ..................................... 426/28; 426/52; 127/38; 127/42; 260/112 G
[58] Field of Search ...................... 426/18, 28, 31, 52; 435/74, 99; 260/112 G; 127/38, 42

[56] References Cited

U.S. PATENT DOCUMENTS

| | | | |
|---|---|---|---|
| 2,583,684 | 1/1952 | Christensen | 435/99 |
| 3,115,410 | 12/1963 | Huffman | 252/316 |
| 3,791,865 | 2/1974 | Hurst et al. | 127/32 |
| 3,998,696 | 12/1976 | Yomoto et al. | 435/99 X |
| 4,012,333 | 3/1977 | Towle | 426/573 X |
| 4,042,414 | 8/1977 | Goering et al. | 127/32 |
| 4,069,103 | 1/1978 | Müller | 435/99 X |
| 4,116,770 | 9/1978 | Goering et al. | 435/99 X |
| 4,125,528 | 11/1978 | Rao et al. | 260/112 G |
| 4,154,623 | 5/1979 | Schwengers et al. | 127/39 |
| 4,311,714 | 1/1982 | Goering et al. | 426/28 |

FOREIGN PATENT DOCUMENTS

652194 4/1951 United Kingdom.

OTHER PUBLICATIONS

C. C. Calvert et al., "Waxy vs. Normal Barley in Rat and Pig Diets", Chem. Absts., vol. 86, No. 19, p. 437, No. 138444e.

M. A. Anderson et al., "Enzymatic Determination of 1,3″1,4-A-Glucans in Barley Grain and Other Cereals," Journal of the Institute of Brewing, vol. 84, Jul.-Aug. 1978, pp. 233-239.

W. Banks et al., "Studies on the Starches of Barley Genotypes: the Waxy Starch", Die Starke, vol. 22, No. 5, May 1970, pp. 149-152.

Noyes, R., "Protein Food Supplements", Noyes Dev. Corp., Park Ridge, N. J., 1969, pp. 276, 277.

*Primary Examiner*—Robert A. Yoncoskie
*Attorney, Agent, or Firm*—Lowe, King, Price & Becker

[57] ABSTRACT

The processing of waxy barley grain by a series of sequential steps to produce a carbohydrate syrup having a high maltose content, novel protein products, a gluten-like product, a barley oil, a carbohydrate gum, all useful in the food industry, and a fermentable product which can be converted to alcohol. The processing steps comprise conditioning and milling of waxy barley grain, separation of starches, conversion of starch residues by liquifaction and saccharification to the syrup and protein products, and recovery of the products and by-products.

37 Claims, 5 Drawing Figures

4,428,967

PROCESSES FOR PRODUCTION OF WAXY BARLEY PRODUCTS

CROSS REFERENCE TO RELATED APPLICATION

This application is a continuation-in-part of parent application Ser. No. 047,855, filed June 12, 1979 now U.S. Pat. No. 4,311,714, dated Jan. 19, 1982.

BACKGROUND OF THE INVENTION

1. Field of the Invention

This invention relates to the processing of waxy barley grain to obtain valuable products therefrom and more particularly, to the processing of waxy barley grain for the production of a carbohydrate syrup high in maltose content, a variety of protein products, a fermentable product suitable for conversion to alcohol, a carbohydrate gum and novel uses for these products.

2. State of the Art

Barley is a grain product which has been found useful mainly in the brewing industry as barley malt which utilizes the enzymatic activity of the barley malt for industrial applications such as starch-splitting and protein degrading. The barley malt is an important source of alpha- and beta-amylase and is used in many foods such as beer, wheat flour and cereal to convert starch to fermentable sugars. Exemplary prior art showing the use of barley in the formation of malts and the use of malts in the fermentable industry may be found for example in U.S. Pat. Nos. 2,947,667; 3,157,583; 3,446,708 and 4,140,802.

There has been very limited work in the utilization of barley in other areas heretofore. Exemplary of the prior art in which there have been attempts to use barley in other ways may be exemplified by U.S. Pat. No. 3,846,397 which processes grain residues obtained from mashed barley malt to recover water soluble protein products suitable for utilization as animal feeds.

U.S. Pat. No. 1,548,721 is also of interest as it describes the treatment of starch with an ungerminated grain such as barley until the major portion of the starch has been saccharified. However, useful products are not obtained from the barley in this procedure.

U.S. Pat. No. 3,689,277 discloses production of a protein hydrolysate from barley grain by treating with a proteolytic enzyme at 35°–50° C. to produce protein hydrolysis products and a starch fraction, the solution containing at least 40% of protein. The protein is then reacted with sugar to produce a product having a caramel flavor.

U.S. Pat. No. 3,901,725 describes wet processes for separating cereal starch granules according to size and states that barley, rye and wheat starch may be treated in the process. However, the patent does not set forth specific examples of obtaining any product from a barley grain. U.S. Pat. No. 4,094,700 is directed to a method for producing gluten and starch from a dispersion of wheat, barley or rye endosperm fractions in water. However, there is no actual example directed to processing of barley as the starting material or any description of a product obtained from the barley.

A publication entitled "Barley Syrup Production" by the ABMIP/DDS-KROYER Process, Pamphlet No. 815G008E, published by the Danish Company, DDS-KROYER, presented in 1972 in Peking by Erik S. Nilsson, discloses the conventional procedure for processing of barley by conversion to malt through germination of the raw barley. A process is disclosed wherein an extract simulating the extract from barley malt action can be produced by degrading barley directly with enzymes such as alpha-amylase or beta-amylase.

U.S. Pat. No. 3,791,865 discloses maltose syrups obtained from corn starch wherein the syrup contains 60–80% maltose and 15–35% maltotriose.

It is also known from U.S. Pat. No. 3,115,410 to Huffman that a barley fraction having thickening properties may be produced by heat treatment and special milling of barley. Further, U.S. Pat. No. 4,154,623 to Schwengers describes a process for preparing a starch hydrolysate from wheat, barley or rye, but not waxy barley, including hydrating and salting the kernels, wet milling the softened kernels, and separating fibers and pentosans attached thereto, as well as germs and glutens from the wet milled product to form a starch containing slurry essentially free of insoluble pentosans, washing the fraction to form a refined starch containing product and hydrolyzing to form a starch hydrolysate and refining the hydrolysate.

U.S. Pat. No. 4,125,528 is directed to a process of fractionating whole wheat kernels into glutens, starch and bran germ components, but there is no disclosure of application of this process to waxy barley.

Banks et al, "Studies on the Starches of Barley Genotypes: the Waxy Starch"; Die Starke, Vol. 22, no. 5, May 1970, pgs. 149–152; is a study on investigations into the properties of starches of waxy barleys which are materials of the type which may be used as starting materials in the process of this application. The article discusses methods for extraction of starch from two genotypes of Japanese waxy barley, and also contains data with respect to enzymatic degradation and average molecular weight as well as properties.

Anderson et al, "Enzymatic Determination of 1,3:1,4-A-Glucans In Barley, Grain and Other Cereals"; Journal of the Institute of Brewing, Vol. 84, July-August 1978, pages 233–239, is a report of work concerning the enzymatic determination of glucans in barley, grain or other cereals, but there is no discussion of the determination of glucans in waxy barleys.

Calvert et al, Chemical Abstracts, Vol. 86, no. 19, page 437, No. 138444(e), "Waxy vs. Normal Barley in Rat and Pig Diets", is a review of the use of waxy versus normal barley in rat and pig diets.

In none of these prior art references, however, is there any disclosure for the processing of waxy barleys in accordance with the methods of the present invention or the production of novel products described herein.

SUMMARY OF THE INVENTION

It is accordingly one object of the present invention to provide a series of processing steps by which a number of valuable products can be obtained from waxy barley grain, which products have not been known heretofore.

A still further object of the invention is to provide a manufacturing process for treating raw waxy barley grain to produce a carbohydrate syrup which is high in maltose content, and which is useful in numerous areas of the food industry.

A still further object of the present invention is to provide a method for processing of waxy barley grain to produce a high maltose carbohydrate syrup, low, medium, or high protein-content products, some of which have the characteristics of gluten, a barley oil, a by-product suitable for fermentation to produce alcohol, and a carbohydrate gum.

A still further object of the invention is to provide a complete processing system by which these products can be obtained utilizing a continuous procedure whereby the products are obtained in sufficient purity to be used in a wide spectrum of food industry products.

Other objects and advantages of the present invention will become apparent as the description thereof proceeds.

BRIEF DESCRIPTION OF THE DRAWINGS

Reference is now made to the drawings accompanying the application wherein.

DETAILED DESCRIPTION OF THE PREFERRED EMBODIMENTS

Figure 1:
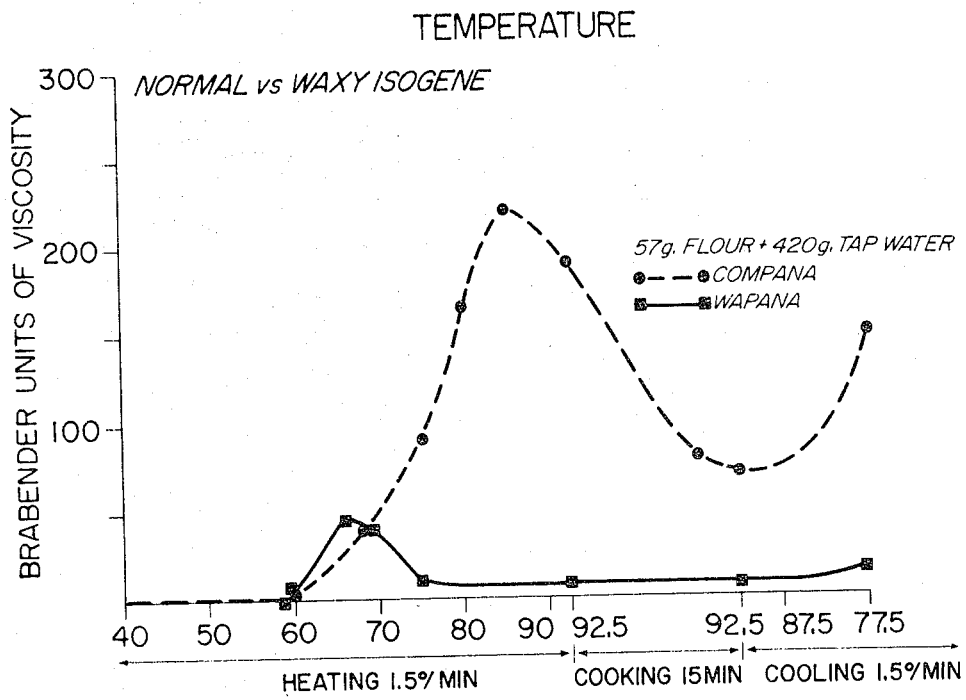
FIGS. 1, 2 and 3 are Brabender curves showing the distinction between the waxy barley flours used as the starting materials in this invention and normal barley flours.

In satisfaction of the foregoing objects and advantages there is provided by this invention a manufacturing process for the recovery of a number of valuable products from waxy barley starting materials or grain, said products comprising at least three different protein products including a gluten type product having a protein content of above about 80% with characteristics making it suitable for bread making and the like; a bleached type protein product with a protein content in the range of about 70–78% which can be obtained in powdered form for use in food grade products, for example, as a substitute for soy protein; and a protein residue containing from about 20–25% protein which is useful for incorporation in animal feeds. Also obtained as a result of the process is a barley syrup having a maltose content in excess of 60% and less than 5% dextrose which can be substituted for corn syrup and/or ordinary sugar in food products as well as a barley oil which can serve as a substitute for corn oil and also as a source of vitamin E. A by-product liquid suitable for fermentation to alcohol is also produced together with by-products such as bran and carbohydrate gum.

The invention described and claimed herein is based on the discovery that a series of novel and valuable products can be produced and recovered from waxy barley by initially hydrolyzing the starch with a beta-glucanase containing enzyme to break the initial viscosity and form a thin paste, then liquefying the starch with an amylase containing anzyme, debranching to debranch amylopectin and partially hydrolyze glucans, and then saccharifying the starch. During the process several useful products are obtained. Important process features include use of small amounts of enzyme, e.g., about 0.25 up to about 1.0% by weight and short conversion times as well as the use of enzymes which contain both beta-dextranase and alpha-amylase activity.

The manufacturing process comprises treatment of waxy barley grain, that is, a barley grain which contains at least about 92% amylopectin, the steps of the process broadly comprising:

(a) obtaining a waxy barley flour or whole barley and mixing with sufficient water to form a paste after removal of inerts, (b) adding to the paste a beta-glucanase-containing enzyme in a sufficient amount to thin the paste and form a slurry and at least partially hydrolyze beta-glucans contained in the flour to place the beta-glucans in a form suitable for separation from the starch, and then gringing the slurry, (c) permitting the enzyme to at least partially hydrolyze beta-glucans contained in the mixture and release protein solids from solution, and thereby form a resulting suspension containing crude starch, protein solids and fiber;

(d) subjecting the suspension to a solids separation step based on particle size by which the protein solids and fiber products are substantially removed from the suspension to provide a starch suspension, (e) adjusting the solids content of the starch suspension to about 25–40 wt% starch solids by removal of excess liquid which comprises a fermentable mill water, and adding to said suspension an enzyme which contains amylase in a sufficient amount to at least partially hydrolyze the starch and form maltose and produce a resulting mixture, (f) cooling the resulting solution and adding a further portion of an enzyme which contains amylase and agitating for a sufficient time to effect additional starch conversion and produce a resulting mixture, (g) heating the resulting mixture at a temperature of about 50° C. to 70° C. to substantially complete starch conversion, and form a mixture of protein solids in maltose syrup, and (h) separating and recovering the protein solids and a liquid comprising a maltose syrup.

The present invention is concerned with a series of processing steps by which a number of novel products are obtained from waxy barley grain which find value in various areas in industry. In particular, the process provides a procedure for producing high maltose syrup, at least three different protein-containing products, bran, a product suitable for fermentation in the formation of alcohol, a barley oil, and a beta-glucan, which is a carbohydrate gum which may be used as a thickening agent in food preparations. The process is directed to the production of these products from waxy barleys, several strains of which are known in the art. The waxy barleys are chemically the same as starch found in waxy varieties of corn but the physical properties of the waxy barley starch are different from those of ordinary corn starch which make it easier and less expensive to process.

Several waxy barleys are described in the prior art, for example in our publications in Cereal Chemistry, 53 (2), pages 174–180, (1975), and Cereal Chemistry, 55, (2) pages 127–137, (1977), as well as our prior U.S. Pat. No. 4,042,414, issued Aug. 16, 1977, U.S. Pat. No. 4,054,671, issued Oct. 18, 1977 and U.S. Pat. No. 4,116,770, issued Sept. 26, 1978. These waxy barleys are produced by cross-breeding barley varieties having different genes as described in these publications. These publications and prior patents describe a barley species which is self-liquifying (Washonupana) and other waxy barleys (Wapana and Waxy Oderbrucker). The disclosures of these publications are hereby incorporated by reference, especially the disclosures which compare waxy barleys with normal barleys. Other species of waxy barleys which may be used as starting materials in the process of the present invention include Watan, Wabet, Washonutan, Washonubet, Wanutan and Wanupana. It should be noted that waxy barleys are usually named with the prefix "wa-", and normally contain about 98–99 wt% of amylopectin. It should be understood that the waxy barley starting material is not limited to those named herein.

Figure 2:
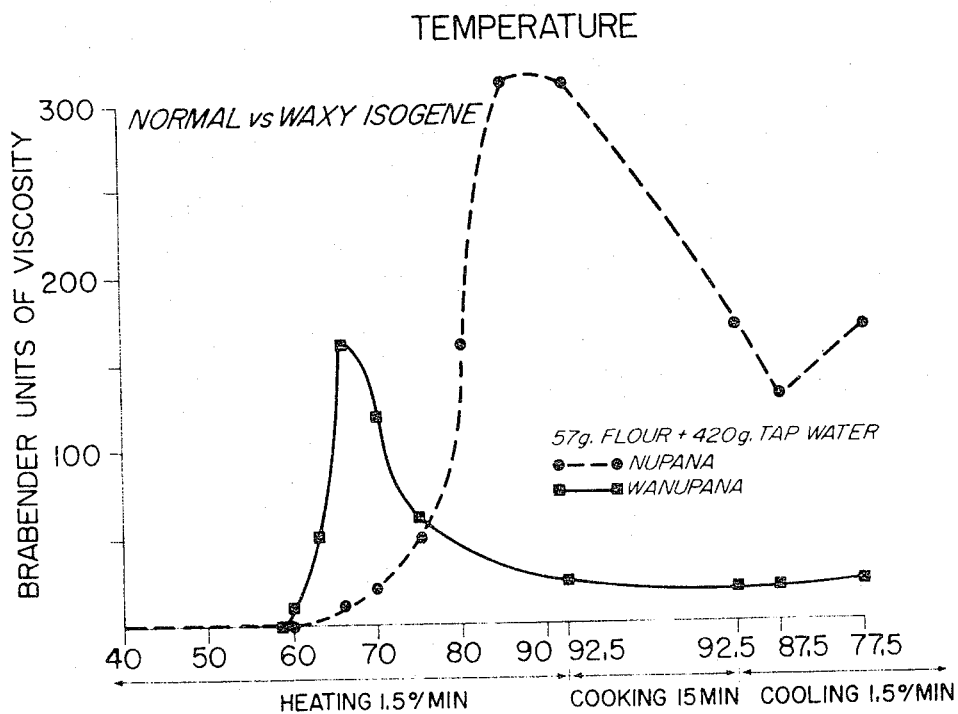
Figure 3:
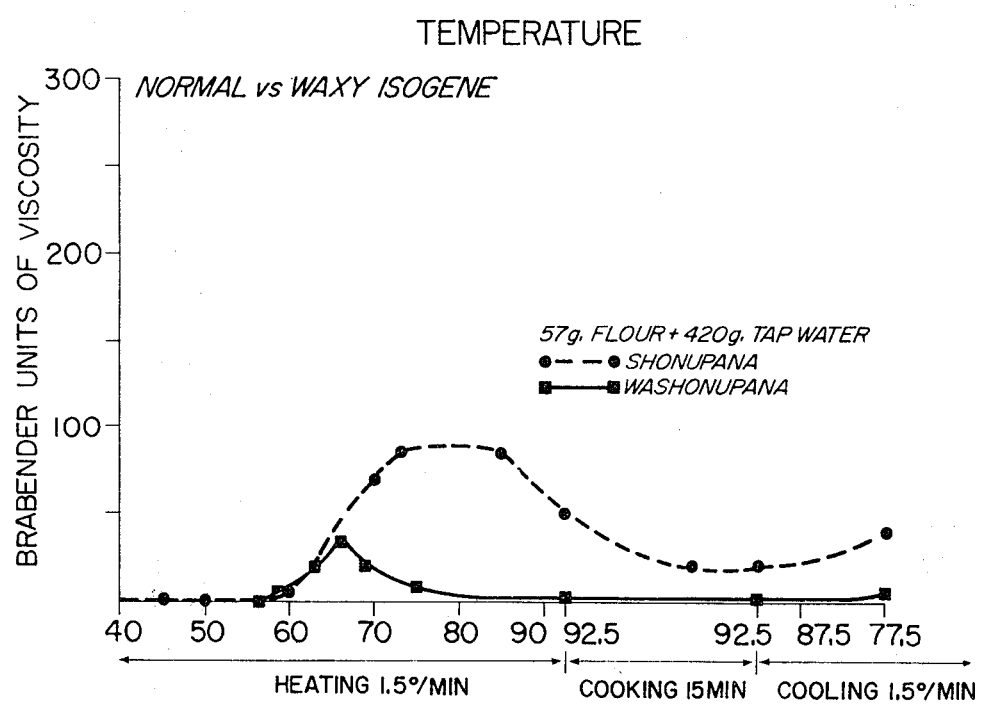

The differences between normal barley and the waxy barleys used in this invention are dramatized in FIGS. 1, 2 and 3 which are Brabender curves of the waxy barleys as compared with normal barleys. These curves show the Brabender units of viscosity which are determined as a result of heating different varieties of waxy and normal barley. In FIG. 1, Wapana is compared with Compana; in FIG. 2, Wanupana is compared with Nupana; and in FIG. 3, Washonupana is compared with Shonupana. A comparison of the viscosities of the waxy varieties clearly show distinct differences in the Brabender unit of viscosity at the different temperatures.

Obviously, any equivalent starting material may also be employed provided that it is a waxy type product which contains less than about 8% amylose, or alternatively, contains at least about 92% amylopectin. It should be noted that a normal barley contains about 72–80% of amylopectin and the major difference between the waxy and the normal barley is found in the amylopectin content.

The process of the present invention produces a number of major products from the waxy barley starting material through a series of novel processing steps. These products may be broadly described as bran, starch, a feed grade product containing about 20 to 25% protein, a food grade product containing about 70 to 78% protein, a food grade product containing above about 80% protein, mixtures of proteins, a barley oil, a syrup containing in excess of 60% maltose, a high carbohydrate soluble fraction or a mill water by-product suitable for fermentation to an alcohol, and a carbohydrate gum suitable for a food thickener. Alternative products may also be produced. For example, if the low protein feed-grade product is combined with a high carbohydrate soluble fraction, also referred to herein as mill water, and this is combined with the wash waters from the starch and protein processing steps, subsequent fermentation of the mixture by conventional methods will produce alcohol and/or Torula yeast with the by-product or dry distillers solubles similar in consistency to the product obtained when one ferments sugar from corn. The alcohol is of course valuable in many areas and particularly for combination with gasoline in the modern fuel sometimes referred to as "Gasohol".

The fermentation of the mill water may be carried out in the conventional manner by the use of enzymes such as yeast.

An important aspect of the present invention is the discovery that milled whole waxy barley can be used as the starting material in the invention rather than waxy barley flour. A further important aspect is that no more than about twenty-four hours is a sufficient period to effect starch conversion. Both of these aspects contribute significantly to the economics of the overall process.

The maltose syrup concentrate can be catalytically reduced to produce maltitol which is a commercial sweetener and could be considered as an optional product to be produced from the barley in addition to those named above. With the distillers solubles, yeast, alcohol, barley oil and maltitol, as well as beta-glucan, this represents a large number of potential commercial products to be recovered from the barley grain. In view of the limited use of barley heretofore, this represents an outstanding contribution to the art of processing barley grain.

Of the several products produced, the bran is useful as a food supplement, particularly with current emphasis on fiber in the diet. The products low in protein content could, of course, be used as animal feeds whereas the high protein containing materials are, of course, useful in various major markets as a substitute for vital gluten which is obtained from wheat. It should be noted that the maltose syrup and the high protein products obtained from the barley according to the present invention are considered to be commercially attractive products hving novel physical and chemical characteristics.

The maltose syrup in essence contains at least about 55% maltose, and preferably contains in excess of 60% maltose and less than 5% dextrose and with proper concentration, may contain up to 80% solids. A typical sugar profile of the syrup is about 3.0 to 3.5% glucose, about 55.0 to 65.0 maltose, about 5.0 to 8.5% maltotriose, and remainder higher sugars. Thus, this type of product is highly desirable and is useful in bakery and dairy products such as cereal, sweeteners, ice cream, and brewing operations as well as hard candy products. For example, in the ice cream industry, the maltose syrup is useful in providing texture for body and crystallinity control.

These products are produced by a multistep procedure comprising processing of the barley grain. These processes are broadly described in FIG. 4 with the starch separation and conversion processes more specifically described in FIG. 5. The initial step comprises selection of the starting waxy barley grain and cleaning at 1 to remove inert particles, dirt and the like, prior to processing, which are passed to waste or by-product recovery by line 2. The grain is then removed by line 2 and in one embodiment, subjected to conditioning and milling at 5 to remove hulls if necessary, and to condition by the injection of a little moisture as by the introduction of steam at 4. It should be understood that in this step, either the hulless barley or barley with hulls can be introduced but any hulls present are preferably removed. In the milling operation of this step, most of the bran and a portion of the germ are removed by this stage to result in a crude flour product.

In a second embodiment, whole waxy barley may be used in place of barley flour. In this embodiment, the whole waxy barley is initially ground in a milling stage. The milling stage is preferably carried out by dry grinding using for example a simple wheat flour mill or a hammermill.

If flour is to be produced, the whole barley is first conditioned by the introduction of steam at 4. A sufficient amount of moisture is introduced as steam to assist in conditioning and milling of the product by forming hydrated chunks which can then be milled.

The crude barley is removed from the conditioning and the milling step by line 7 and transferred to a mixing tank 8 where sufficient water is introduced by line 9 to provide a slurry that can be easily handled. The water is fresh makeup water and/or process recycle water obtained from source 10-a and 10-b introduced by line 11 and line 9. In general, about 3–5 parts of water per part of barley feed are present in the mixing tank. A small amount of enzyme is introduced by line 11a in order to provide beta-glucanase and reduce the viscosity caused by the presence of beta-glucan. By reducing viscosities is meant that the viscosity of the mixture is adjusted to a suitable flow. This is achieved since the beta-glucanase in the enzyme at least partially hydrolyzes the beta-glucans to make them at least partially soluble so they can be removed and the mixture will be thinned. The viscosity is measured by the flow of the mixture or mash through an inverted 100 ml pipette. A workable viscosity is a flow time of about 4 to 12 seconds as measured through the inverted 100 ml pipette. This reduction of viscosity is necessary because the beta-glucan is partially water soluble so that when the ground barley of flour is mixed with water, a highly viscous suspension is obtained.

In the mixing operation or stage 8, milling is carried out on any hydrated chunks to break them down in the slurry and form a fine dispersion. At this point an initial separation and removal by line 12 of a low-grade protein is made, the protein being removed to by-product recovery. This feature is specifically described with respect to FIG. 5.

The starch slurry is then removed by line 13 to what may be broadly described as a starch separation stage at 14. The mill water is removed by line 15 to by-product recovery. The starch granules at this point are centrifuged and removed by line 16 to a conversion and refining stage 17 where, with adjustment of solids contents by water introduction via line 18, and the introduction of additional enzyme or green malt as required by line 19, novel protein products and maltose are obtained. The starch separations and conversion and refining operations are more specifically described in FIG. 5.

In this step, the added enzyme contains amylase, and preferably alpha-amylase and beta-amylase for starch conversion so that maltose is produced. In one feature of the invention, the enzyme may be a green malt which also contains beta-glucanase to partially hydrolyze the beta-glucans contained in the barley starch. After the production of these substances, any proteins released are removed by line 20 to by-product recovery and further processing. The syrup produced by conversion of the starch and which contains the maltose, is removed by line 21 to product recovery 22. Condensate from the conversion and refining procedures are removed by line 23. The wash waters and other by-product liquors are removed by line 24 and recycled.

The by-products recovered from the starch separation 14, and conversion and refining stage 17, are passed to by-product recovery 25 as shown where appropriate processing takes place to recover the several by-products from the operation. The by-product procedures are discussed more specifically with respect to FIG. 5. In general, solids contents are adjusted, additional enzyme is added to substantially complete the hydrolysis of the remaining beta-glucans, and together with separating techniques, result in removal of at least one protein product high in protein content at 30 by line 29. As may be seen, steam for heating and solids content adjustment of the fermentable fiber cake and protein cake are added by lines 26, 27 and 28, respectively. In addition, a mill water or carbohydrate water is removed by line 31 to recovery 32 which is a fermentable mixture suitable for conversion by conventional fermentation procedures to alcohol or other products. The fiber cake is removed from the system by line 33 to cake recovery 34 and roughage such as hulls and cracked grain are removed by line 35 to recovery 36. Condensate is removed by line 37 and may be recycled by line 37.

Mother liquors and wash waters from this by-product recovery 25 are recycled as necessary or required via line 38. Beta-glucan is removed by line 39 and recovered at 39a.

Since production of the various mill waters and fermentable liquids require considerable water use and it would be desirable to reduce water consumption, the present invention provides a method whereby this can be effected. It was observed that this water will become acidic when allowed to stand due to the lactic acid forming bacteria naturally present in the grain. For this reason, it was decided to pasteurize it by heating to a temperature in the range of about 60° to 80° C., preferably about 70° C. and holding at that temperature for about 5 to 20 minutes to effect pasteurization. The low temperature was used to prevent the denaturation of any protein present in the mill water. The pasteurized mill water was passed through a Westfalia centrifuge which removed the solids and the supernatant was recycled to treat another batch of ground barley. Thereafter, on standing, it was found that the pasteurized mill water remained stable as the pH remained constant during storage indicating this pasteurization treatment was a complete success and would not create any problems in a large scale commercial operation. Using this process, it was possible to reduce the water consumption from 4 parts water to 1 part barley to a value of 1 part water to 1 part barley. The only limitation was the amount of water held by the screen residue and the crude starch. It is necessary to press the excess water out of the screen residue to reach this low level; however, that technique would also be used in a large scale plant to reduce the cost of drying this bran-protein fraction.

The amount of dry solids removed by this process averaged 2.4 pounds per 100 pounds of barley. It was removed as a 30% solids residue which on drying was found to be 60% protein and 17.5% ether extractables. After extraction of the lipid the residue contained 73% protein.

It was also discovered that if protein fractions recovered are washed or extracted with a lower alkyl alcohol, preferably ethyl alcohol, the alcohol will extract unsaturated vegetable oils from the protein. This results in a more stable protein and also provides a useful barley oil.

Figure 4:
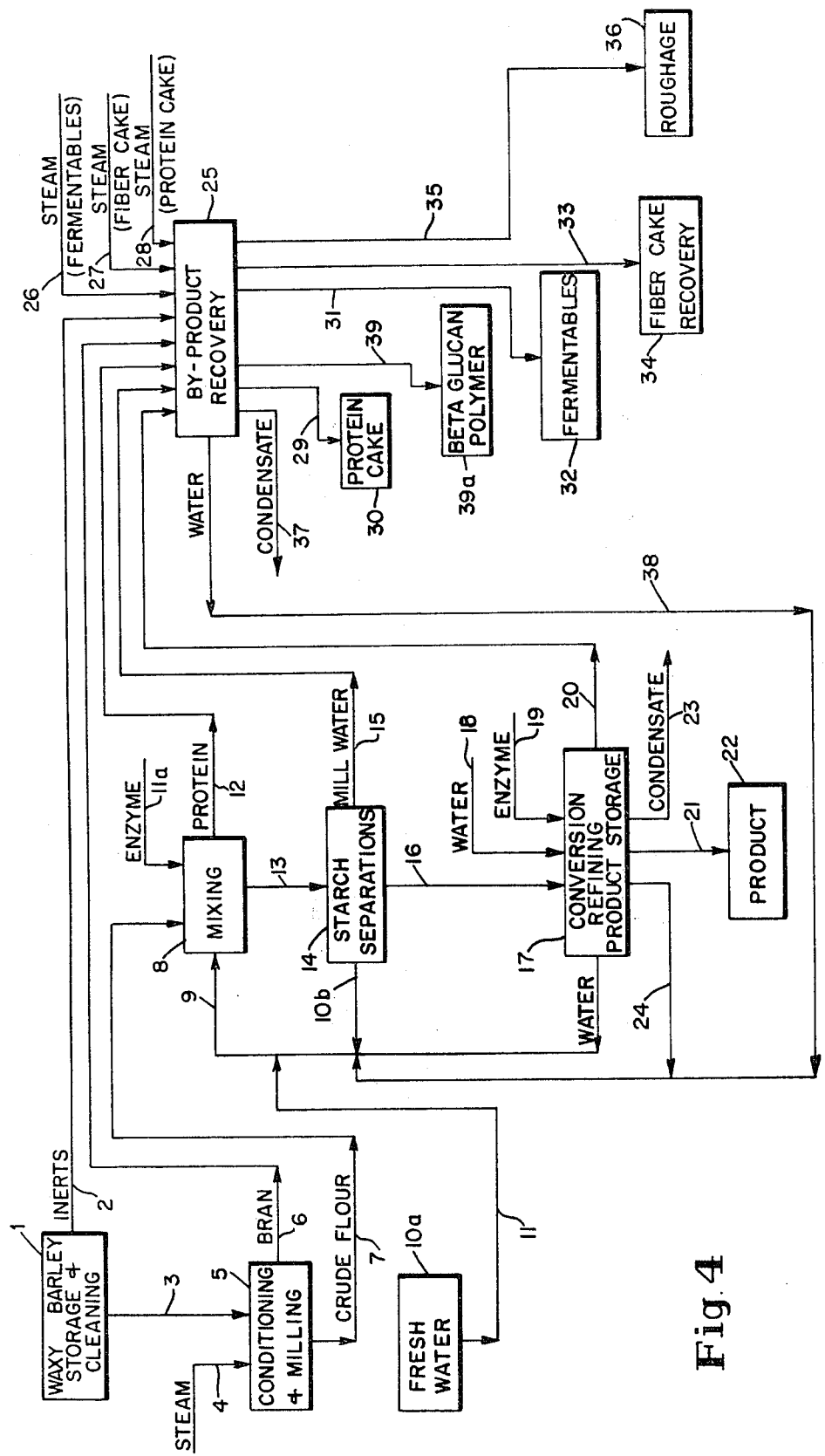
FIG. 4 shows a complete schematic flow sheet for a commercial processing system of the present invention.
Figure 5:
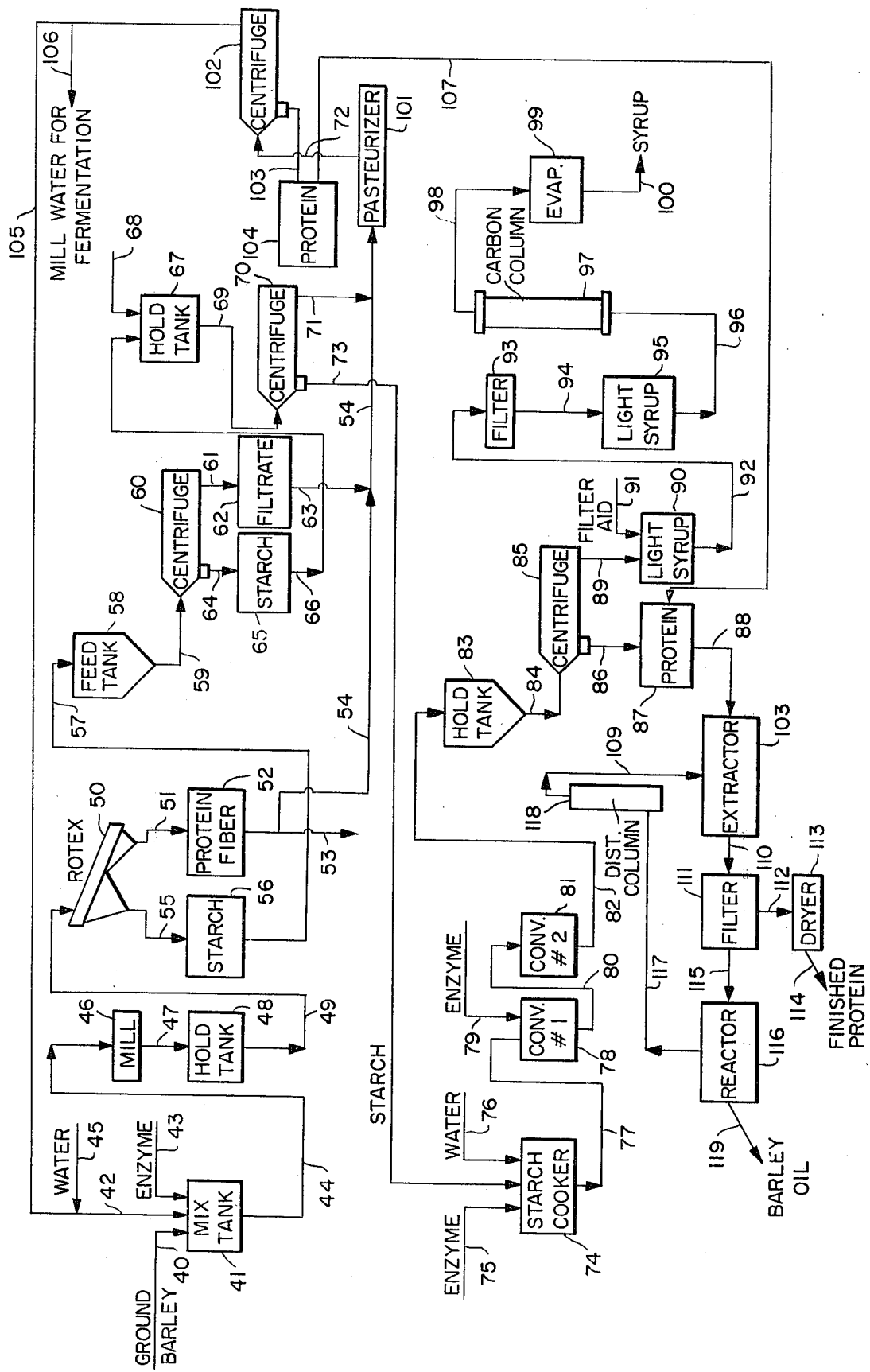
FIG. 5 is a flowsheet showing details of the starch separations and conversions and recovery of products.

The schematic diagram of FIG. 4 shows the broad steps and parameters of the process of this invention by which the several useful products are obtained. FIG. 5, however, sets forth specific embodiments for conducting the process, particularly with respect to the starch separations and conversions and product recovery, and alternative procedures.

Referring now to FIG. 5 which in essence is an actual pilot plant run, it will be seen that the process begins with the mixing step and is followed by the starch separation, conversion, and product recoveries occurring thereafter. In the diagram of FIG. 5, the whole barley or barley flour is introduced by line 40 into mixing tank 41 provided with agitation, together with sufficient recycle water by line 42 and fresh water by line 45, if needed, to convert the barley to a thin paste. If barley flour is used, the bran and inerts are removed prior to formation of the paste. However, if whole barley is the starting material, the bran is removed with the screen residue as described hereinafter to provide a bran-protein. Generally, about 1 to 5 parts of water per part of barley are added. At this stage, prior to grinding, there is also added a sufficient amount of an enzyme, preferably green barley malt by line 43, to partially hydrolyze the beta-glucans present and to reduce the viscosity to workable levels. This enzyme is an enzyme which contains beta-glucanase to break down glucans so that they will solubilize and thin the mixture or lower the viscosity. In general, it may be said that there is added sufficient beta-glucanase containing enzyme, e.g., green barley malt or equivalent material, at this stage to lower the viscosity of the slurry to a workable viscosity in about 1 hours time. The enzyme or green barley malt contains beta-glucanase which at least partially hydrolyzes the beta-glucans present in the barley. The beta-glucans are substances which make the barley difficult to work with and it is therefore expedient to partially hydrolyze and remove them at this stage of the process.

The enzyme added is preferably a green malt such as waxy barley green malt since one needs the debrancher and all the beta-glucanase that can be added in order to partially hydrolyze as much of the beta-glucans as possible without the addition of any normal barley starch which has a higher pasting temperature. Dry malt is operable but a substantially larger quantity would be required and maltose yields would be less. In a preferred embodiment, the enzyme will also contain $\alpha$-amylase so that starch conversion can be initiated. By green malt is meant that it is freshly made and not kilned malt. It is also possible to add a commercial bacterial amylase or enzyme rather than the green malt, but the material to be added will be dictated by economics and should be based on the least amount of material necessary to saccharify the starch and which is effective to remove the glucans. Products which can be used in place of the green malt are a commercial product sold as Cereflo 200 L which is an industrial bacterial beta-glucanase preparation produced by fermentation which will thin the starch and hydrolyze the beta-glucan and Wallersteins Malt Enzyme PF which will furnish the amylases to conversion of thinned starch to sugars, available from Wallerstein Company.

The resulting slurry is then removed by line 44 and subjected to a milling operation by passing through a conventional mill such as buhr mill 46. In the actual operation this process is repeated two more times. The buhr mill is a conventional device that is simply effective to grind the slurry to break up hydrated chunks. The ground material from the mill 46 is transferred by line 47 to a holding tank 48 which is provided with agitation to maintain the slurry in suspension and permit the enzyme to work. The mixture is then pumped via line 49 to a vibrating Rotex screen or similar device 50, where a separation is made between the starch product and the protein based on particle size. If whole barley is the starting material, this product is a bran-protein. At this stage, the protein solids or bran protein solids are continually removed by line 51 to container 52, together with some of the liquid, referred to herein as mill water, from the protein fiber separation. In actual practice, the protein or bran-protein material is recycled two more times in sequence with the previously described milling operation until the protein has minimal starch content. The residual protein-fiber residue is washed and dried to produce a barley gluten feed containing 20–25 weight percent protein content. The protein-fiber residue is recovered at line 53. Process water or mill water from this separation from line 54 is treated as described hereinbelow.

The starch is removed from separator 50 by line 55 to container 56 and then passed via line 57 to feed tank 58 and then via line 59 to centrifuge or equivalent separator 60 to obtain a starch slurry with 40–60% by weight starch solids and a filtrate solution. The filtrate or mill water is removed by line 61 to container 62. Thereafter, this mill water is removed by line 63 and mixed with the mill water from the protein-fiber separation in line 54. This mixture of mill water is then combined with additional process liquids from subsequent centrifuge steps and treated as described hereinafter.

The total recovered starch in line 64 from centrifuge 60 is transferred to container 65, washed, and then transferred by line 66 to holding tank 67. Water may be added by line 68 as necessary to adjust solids content. The starch is then removed at line 69 to centrifuge 70. Process liquids from the centrifuge including any wash waters, are removed by line 71 and combined with the liquids in line 54 for processing and recycle as described hereinafter.

The refined starch is then passed by line 73 to a jacketed agitated cooking vessel 74 for starch conversion with additional enzyme from line 75. Water is added via line 76 to obtain a starch solids concentration in the range of 25–40 weight percent basis, most preferably about 30%.

At this point the pH of the starch in the cooker should be in the range of 5.5 to 6.0, preferably about 5.6–5.8, but it may be necessary to adjust the pH to within the desired range as by the addition of sodium hydroxide. Also, to the resulting mixture is added about 0.5% by weight of green malt or other $\alpha$-amylase-containing enzyme, based on the dry weight of starch, by line 75 and the contents are constantly agitated. The pH-adjusted mixture is then subjected to heating in the temperature range of about 60 to 76° C., most preferably at 75° to 76° C., until the starch dissolves and there are no starch granules remaining in the mixture. This normally requires a period of from about 5–5 minutes, preferably about 10 minutes. Additional water may be added if necessary through line 76. It is important that the temperature be maintained relatively near to the 60°–76° C. range because if the temperature goes too high, it could adversely affect the waxy barley gluten and it should be above 60° C. for the enzyme to work. At the conclusion of this stage, the starch is degraded to the point where it gives little if any iodine color thus indicating that there are no longer any long chain residues present. Glucose polymers with more than 12 glucose units will give an iodine color. This is an important aspect since the same treatment will not give the same results with other grains, even regular barley. A very important aspect of the present invention is that total starch conversion can be achieved in less than about 24 hours. In fact, a particularly important feature of the present invention is that the process can be carried out to produce a medium conversion syrup in a time period of 2 to 3 hours. This syrup will comprise a composition of 2–3% glucose, 48–50% maltose, 4–6% maltotriose, and 40–42% highers. Production of a medium conversion syrup of this type is illustrated in the working examples. This is an unexpected advance in this art in view of the small amounts of enzyme required and short time periods. The resulting syrup competes favorably with several commercial grades of syrup.

At this point, the mixture is removed from the cooker 74 by line 77 and passed to the No. 1 converter 78. The temperature in converter No. 1 is reduced to about 35°–55° C., preferably about 40° C. and a further portion of about 0.5 wt% green malt or equivalent enzyme is added through line 79. In this stage the solution is held at the indicated temperature of about 40° C. for about 1 to 4 hours with continuous agitation. While it is theorized that in converter No. 1, the debrancher in the enzyme is effective in debranching the amylopectin and in partial hydrolysis of beta-glucan, applicants do not intend to be bound by this theoretical explanation as a sole basis for its action.

The resulting solution is then passed by line 80 to No. 2 converter 81 where the mixture is maintained at a temperature of 50°–70° C. for about ½ to 2 hours. Preferably, the solution is maintained at about 60° C. for 1 hour or sufficiently long for the viscosity to become low enough to centrifuge the mixture. At this stage the crude gluten from the barley will be released and the mixture is then centrifuged to remove the crude protein from the syrup filtrate. To do this, the mixture is passed by line 82 to holding tank 83 and then via line 84 to centrifuge 85. In the centrifuge, the crude protein is removed by line 86 to container 87.

In the meantime, the mill water in line 54 from protein fiber separation 52 and centrifuges 61 and 71, is passed through pasteurizer 101 and then transferred to centrifuge 102 via line 72 where a high protein, high fat product is removed by line 103 and collected at 104. The process liquids or mill water from centrifuge 102 are removed via line 105 and recycled to the mix tank 41. A portion of the mill water may be removed by line 105 for fermentation. This material is transferred via line 107 to container 87 to be mixed with protein from centrifuge 85. This mixed protein is transferred via line 88 to extractor 108, ethyl alcohol is added via line 109. After mixing, the material in 108 is transferred via line 110 to filter 111 where protein solids are removed via line 112 to dryer 113 producing finished protein via line 114. This protein is 70–75% protein and low in fat. The filtrate from filter 111 passes via line 115 to reactor 116 which removes the alcohol vapor via line 117 to column 118 where 95% alcohol is recovered and recycled via line 109 to 108. Barley oil is removed from reactor 116 via line 119.

In an alternative embodiment (not shown), after centrifuging and removal of crude protein, the mixture may be returned to Converter No. 2 and held for an additional time to lower the viscosity, so that the beta-glucan can be removed with a supercentrifuge. The resulting product can be spray dried to produce a carbohydrate gum in yields of 1–3% of initial barley weight. The carbohydrate gum is believed to be a waxy barley beta-glucan polymer consisting of a series of glucose units hooked together through a beta-linkage and is probably a mixture of polymers. The gum is characterized by its ability to produce a high viscosity in relatively dilute aqueous solutions, similar to lower or medium viscosity cellulose gums. The gum product is generally tasteless and its gum characteristics make it suitable as a low calorie thickening agent for the food industry such as in salad dressings.

In a separate aspect, the separated crude protein may be washed with water and solubilized in an aqueous solution of lactic acid having a pH of about 4.0. The suspension is then centrifuged and on freeze drying a 66.5% protein product is obtained not having the characteristic properties of gluten. This fraction makes up 38% of the total protein recovered at 88. This protein has a great affinity for water and will produce a gel containing 85% water. The pH is then adjusted to 6.0–6.5 with sodium hydroxide, and centrifuged to remove gluten which on freeze drying yields a product containing 89.3% protein. This fraction makes up 59% of the protein recovered at line 88.

In the meantime, the light syrup obtained from the centrifuge via line 89, which is still at a temperature of about 60° C., is held from 12–48 hours until maximum maltose content is obtained and then a filter aid is added to the resulting mixture by line 91 and the mixture removed by line 92 and filtered at 93 to remove residual solids. The resulting sparkling light tan syrup is then removed by line 94 from the filter 93 to container 95 and then subjected to decoloration by passing through line 96 to a carbon column 97 to obtain a clear syrup. The clear syrup is passed by line 98 to concentrator 99 where the syrup is concentrated by heating and then recovered at 100. The resulting concentrated syrup contains about 2–5% glucose, about 60–65% maltose, with a total solids content in the range of about 80%. Preferably, concentration is carried out by continuously feeding the syrup to multi-effect spray film evaporators for concentration to the final product containing about 80% solids. A recycle loop may be provided for light syrup that does not meet with quality control standards for clarity or composition. This is the maltose syrup product produced in accordance with the invention.

As a result of additional experimental work, it is recommended that the mill water be treated in the following manner to recover useful products.

The mill water from the centrifuge which separates the starch is passed through a jet heater which heats it to 70°–75° C., then it is held for 10 minutes at this temperature by passing it through an insulated pipe with sufficient volume so that it takes about 5–15, preferably 10 minutes for the plant stream to fill it. At this point it is discharged into a centrifuge, e.g., a Westfalia centrifuge, where the solids are removed and then through a heat exchanger to reduce the temperature to 50°–65° C., preferably about 60° C. The stream is then divided according to dictates of plant operation and part of it goes to the fermentors where a little additional enzyme is added to convert the small amount of starch dextrins present into fermentable sugars and the balance goes back into the plant stream where it is mixed with ground barley and sufficient fresh water to meet the total liquid requirements. Fermentation is by conventional methods to convert the sugars to alcohol.

A convenient procedure for conducting the fermentation is to treat the mill water containing the sugars with an enzyme in the conventional manner to produce ethyl alcohol.

The data from the experimental work indicates that the mill water stream after centrifugation will have 5% available sugar. In the pilot plant we were unable to press the bran-protein fraction. This would reduce its moisture content from 80–82% down to approximately 50%. On the basis of the average amount of wet bran-protein obtained in the pilot plant runs, this would have reduced the required fresh water in the three cycles by an additional 23%.

Although this material could be fermented directly, it would be more desirable to increase the sugar concentration somewhat so that the cost of the alcohol recovery could be reduced. Therefore, the mill water will be supplemented by one of the following procedures:

(1) Addition of maltose syrup which does not meet specifications for food and beverage purposes.

(2) Addition of medium conversion syrup produced by 2-3 hr. conversion.

(3) Addition of syrup obtained from washing food protein. This protein when separated from the syrup at 36-40% solids contains 40% sugars. If this protein were washed free of sugars by the use of a horizontal rotary vacuum filter this sugar could be obtained in a fairly concentrated solution.

(4) If the bran-protein (screen residue from the Rotex) does not find a market as human food this residue could be treated to remove the starch and sugars adhering to the bran and fiber. From Table VIII it is observed that these fractions contain from 20-33% starch and from 6-15.7% soluble sugars. This starch and sugar can be readily removed by heating this material to 70°-75° C., holding 10 min, cooling to 60° C., adding a small amount of α-amylase from any source, holding 1 hour, screen and press liquid from solid residue. The screen liquor would be added to the mill water. The solids would be dried for livestock feed. The removal of 30-35% solids should increase the protein content by a corresponding amount.

The mill water will be adjusted by one of the above procedures to a sugar content of 12-16% and fermented using recycled yeast while maintaining at a temperature of 30° C. Since the liquid is free of suspended solids, the fermented beer can be centrifuged before going to the stills to remove the yeast. The recovered yeast will be recycled to the fermentors. This would allow the use of massive yeast populations which are expected to shorten the fermentation time from the usual 60-72 hrs down to 12-14 hrs. This should reduce the required fermentor volume by a factor of 4 to 5 and thus substantially reduce the cost of producing alcohol.

Any excess yeast produced by this system could be added to other residues to improve their value for feed.

It will be appreciated that this process produces a number of major waxy barley products including bran, barley oil, the several grades of protein, the high maltose containing syrup, the fermentable product and carbohydrate gum. The manufacture and recovery of these products from waxy barley thus provides a wide variety of products from a grain which heretofore has not been used for any commercial products.

The following examples are presented to illustrate specific embodiments and best modes of the process of the present invention. However, the process of the invention is not to be considered as limited to the embodiments of these examples. In the examples and throughout the specification, parts are by weight unless otherwise indicated.

EXAMPLE I

Starch Conversion-Ref. Actual Pilot Run

In this example, 0.5 wt% waxy barley green malt was added to starch cooker 74 containing waxy barley Washnupana starch from centrifuge 72 added by line 73. Sufficient water was added by line 76 to make the mixture about 30% starch solids. The mixture was heated with agitation until the temperature reached 75° C. and held for 10 minutes. At this point the material was transferred by line 77 to converter No. 1 where the temperature was dropped to 40° C. and held at this temperature. An additional 0.5 wt% of waxy barley green malt was added and the mixture continuously agitated. After 4 hours the mixture was transferred to converter No. 2 where it was maintained at 60° C. for the balance of the run. Samples were taken at various time intervals following the malt addition:

1 hour, 2 hours, 4 hours, 12½ hours, 24 hours, 36 hours, and 60½ hours. Each sample was cooled quickly by immersing the glass sample bottle (2 oz.) in running water at 3° C. The samples were prepared for HPLC analysis in the following manner:

(1) Centrifuge for 20 min. at 16,300×g to remove protein, glucan, etc.
(2) Decant supernatant and place in boiling water bath for 30 minutes to inactivate enzymes (Note: There may be a short "burst" of enzyme activity as the refrigerated sample is heated.)
(3) Dilute sample 4-fold with doubly distilled water.
(4) Deionize with Amberlite MB-3 resin.
(5) Centrifuge for 15 min. at 12,000×g.
(6) Filter through a 45 Millipore filter.

Samples for total carbohydrate (Phenol/$H_2SO_4$ using a glucose standard) and glucose (glucose oxidase method) were taken after step (2) above.

A portion of each syrup was tested for dextrin color by layering aqueous $I_2$/KI onto the syrup. The 1 hr. and 2 hr. samples stained dark opaque brown; the 4 hour sample stained dark brown, but did transmit some light; the 12½ hr. sample had only a faint trace of iodine stain.

No provision was made for evaporation loss, so the total carbohydrate reflects both changes due to solubilization of starch/dextrins/glucans and also evaporation of water. After the 48 hr. sample was taken, an arbitrary amount of water was added to thin the syrup as it was becoming too heavy (46.5% total solids). The values for total carbohydrate on the following table were measured using a glucose standard and expressed as maltose. The % glucose is present as total carbohydrate based on wet chemistry.

| Time After Enzyme Addition | Measured D.E.*[1] | Calculated (Theoretical) D.E. | Glucose % | $DP_2$ %*[2] | $DP_3$ %*[3] | Highers % | Total Carbohydrate Expressed as Maltose (mg/ml) |
|---|---|---|---|---|---|---|---|
| 1 Hr. | 33.3 | 42.8 | 1.1 | 74.5 | 6.3 | 18.1 | 291 |
| 2 Hr. | 31.1 | 29.2 | 1.1 | 39.9 | 3.8 | 55.2 | 300 |
| 4 Hr. | 33.8 | 31.6 | 1.2 | 45.7 | 4.4 | 48.7 | 309 |
| 12½ Hr. | 38.2 | 36.7 | 2.4 | 55.6 | 6.1 | 35.9 | 331 |
| 24 Hr. | 38.9 | 41.0 | 3.7 | 63.6 | 6.9 | 25.8 | 350 |
| 36 Hr. | 39.6 | 42.3 | 4.1 | 64.9 | 8.9 | 22.1 | 406 |
| 48 Hr. | — | 39.4 | 4.6 | 57.3 | 6.7 | 31.4 | 462 |
| 60¼ Hr. | 40.7 | 40.6 | 5.0 | 59.1 | 7.5 | 28.4 | 416 |

[1] D.E. — Dextrose equivalent
[2] $DP_2$ — Degree of polymerization - two glucose units
[3] $DP_3$ — Degree of polymerization - Three glucose units As will be seen, this Example shows the increase in total carbohydrates expressed as maltose as the enzyme is given opportunity to work in effecting the conversion in the starch conversion stage. After 1 hour the total carbohydrates was 291 parts, whereas after 60½ hours the total carbohydrates had increased to 416 parts.

EXAMPLE II

This example is an experiment directed to barley bran fermentation wherein 150 grams of the bran, and 300 milliliters of water were combined into a very heavy paste and 0.15 milliliters of Cereflo 200L were added while maintaining the bath at 70° C. While heating to 62° C. the mixture had thinned appreciably but on continued heating to 70° C., a paste was formed. The mixture was then cooled to 63° C. and 0.5 wt% of waxy barley green malt added together with an additional 50 milliliters of water to decrease the pasty nature of the mixture.

After allowing to stand overnight at 60° C., the resulting mixture, which had liquified, was screened on a 115 mesh screen and pressed as dry as possible to obtain 187.3 grams of wet solids which dried to 66.2 grams. Baker's yeast was added to the liquid obtained from the pressed screenings. Correcting for sugars contained in the dried grain, a recovery of 21.5 grams of alcohol was obtained from the process. Calculations on this experiment are as follows:

The $CO_2$ loss was 20.4 grams and the total fermentables equal $CO_2$ loss+alcohol, which is equal to 20.5+20.4=41.9 grams. The percent of barley bran fermentable equals $$\frac{41.9 \text{ g}}{(150 \text{ g} - 18 \text{ g H}_2\text{O})} \times 100 = 31.6\% \ (db).$$

The nonfermentable solids from 150 grams of crude barley bran amounted to 39.2 grams.

EXAMPLE III

This example shows a batch process for the separation of proteins from the starch mixture. In this process the starch is separated and added to sufficient distilled water to provide a 30 wt% starch slurry. Then 0.5 wt% of waxy barley green malt is added based on the estimated dry weight of the starch. The resulting mixture is heated to 75° C. for 10 minutes. The mixture is then cooled to 40° C. and an additional 0.5 wt% waxy barley green malt is added and held for 3 hours at 40° C. The mixture is then heated to 60° C. and held until the viscosity, as measured by a 100 milliliter pipette, was 10 seconds or less, which in this case required 1 hour. The resulting mixture was centrifuged on the Bird centrifuge and a protein removed which appeared much dryer than when removed at the end of the initial conversion time. The protein was washed in water to remove enzymes and sugars, frozen and stored. It was found to have elastic properties and to be chewable.

The protein was solubilized at a pH of 4 with lactic acid solution, centrifuged to remove insoluble protein and reprecipitated by adjusting the pH to 6.5 with sodium hydroxide. A portion of the protein was dried in a vacuum oven, and this material, when ground and mixed with water, again hydrated and formed an elastic material. Therefore, the characteristics and properties indicate that it is a gluten product. A more refined product is obtained by dissolving in lactic acid, centrifuging to remove any suspended material and reprecipitating followed by freeze drying the product.

EXAMPLE IV

Using the system described in FIGS. 4 and 5 in this embodiment, the grain selected is Washonupana waxy barley with the total charge to the system being 643.9 parts of dry barley with 87.8 parts of water. After cleaning, to remove straw and roughage, the resulting mixture contains 640.9 parts of barley and 87.1 parts of water and this mixture is then subjected to conditioning by the addition of 1600 lbs/hr. of steam and 500 lbs/hr of water for a time sufficient to break down chunks in the slurry and form a dispersion. The bran and a part of the germ are then removed to by-product recovery. The resulting crude flour contains 564 parts of flour and 61 parts of water and is then passed to mixing where 987 parts of water and 0.5 wt% of green Washnupana waxy barley malt are added to the mixture to hydrolyze beta-glucans present in the barley. After 1 hour, the milled product is screened and a screen residue removed from the system which analyzes when dried as 21.0 wt% protein, 5.1% moisture, 3.1% ether extractables, 2.5% ash and 7.7% crude fiber. The protein residue is washed, centrifuged, and beta-glucan separated.

The crude starch removed from the mixing operation comprises 444.4 parts of starch and 943.6 parts of water and analyzes when dried as containing 17.4% protein, 6.4% moisture, 1.9% ether extractables, 0.76% ash and 0.31% fiber.

The starch portion is washed and then centrifuged and a separation made between the starch granules and the filtrate. The filtrate is removed on the third pass and comprises process liquids or mill water in condition for fermentation to produce alcohol and distiller dry solubles.

The starch fraction, which comprises a mixture of 376.1 parts of starch and protein and 220.9 parts of water, is passed to the conversion stage in a stirred container, and the pH is adjusted to a range of 5.6 to 5.8 by the addition of sodium hydroxide. Sufficient water is added to the mixture to bring the solids content to 30 wt% and an additional 0.5 wt% waxy barley green malt is added to thin the starch while heating the mixture to 75°–76° C. for 10 minutes. The amount of water added at this point is 334 parts.

After heating for 10 minutes the starch dissolves and the solution is then cooled to 40° C. and held for 4 hours with the addition of a further 0.5 wt% of waxy barley green malt under continuous agitation. It is then heated to 60° C. and held until the viscosity decreases sufficiently to centrifuge. The mixture is then centrifuged to separate crude gluten from the light syrup. The syrup portion is returned to the holding tank at 60° C. for 1 hour and then supercentrifuged to remove the beta-glucan gum. After separation of the beta-glucan gum the syrup is returned to converter No. 2 and held until optimum maltose content is achieved. The crude gluten is washed with water, and dispersed in an aqueous solution of lactic acid at a pH of 4.0 which dissolves the gluten. The insoluble protein is removed by centrifugation and the solubilized gluten precipitated by adjusting the pH to 6.0–6.5 with sodium hydroxide. This material is freeze dried to produce a gluten product containing 89.3% protein and makes up 59% of the total crude gluten fraction. The lactic acid insoluble fraction makes up 38% by weight of the total crude gluten protein and on freeze drying contained 66.5% protein. This protein shows a high affinity for water as the freeze dried material will readily form a gel containing 85% water.

In the meantime, to the light syrup removed from the centrifuge, while still at 60° C., is added a small amount of the filter aid and the mixture subjected to filtration. The resulting light syrup is sparkling light tan in color and is then subjected to decolorizing in a carbon column and the resulting clear syrup is subjected to concentration in a multi-effect falling film evaporator to provide a finished product containing 80% solids which analyzes at 60–65 wt% maltose, and 2–5% glucose.

The analysis described in the above specific embodiments of this application were based on standard tests of the Association of Official Analytical Chemists as set forth in "Official Methods and Analysis", 12th Edition. The specific tests used included the following tests:

Protein—Test No. 7.016, page 130;
Ether Insolubles (Crude Fat)—Test No. 7.045, page 135;
Crude Fiber—Tests No. 7.05–7.054, pages 136–137;
Ash—Test No. 7.010, page 130;
Moisture—Test No. 7.003, page 129.

EXAMPLE V

This example sets forth the procedures, conditions and results of a series of pilot plant experiments designed to demonstrate variables in the invention and produce products in quantity.

Procedure

The procedure followed was as described above in the drawings. The ground barley or barley flour was mixed with water (4 parts water:1 part barley by weight) and Cereflo 200L (0.1 U/g. barley) or an extract of green malt. The slurry was stirred gently for about an hour, then milled in a buhr mill and screened on 80 mesh screen on the Rotex. The starch was removed by the Bird centrifuge. The supernatant and the screen "overs" were combined and again milled in the buhr mill, screened and centrifuged. This procedure was repeated a third time. At the end of this step, there were three fractions of starch, the screen residue (bran protein fraction) and the supernatant, or mill water.

The starch fractions were cooled as soon as collected. In the early runs this was done in a walk-in cooler, but because of the proclivity of the starch for souring, it was found best to put the starch in a freezer to drop the temperature quickly, then transfer it to a cooler. This step would not be necessary in a plant running continuously.

An extract of green (unkilned) malt was used for liquefaction and saccharification. Green malt is a rich source of α-amylase and several other enzymes, namely β-amylase, β-glucanase and an α-1,6 debranching enzyme, important for the production of high maltose syrup from waxy barley. Green malt rather than kilned malt was used because the kilning process reduces or destroys some of the enzymes, develops a strong malt flavor in the product, and requires large amounts of energy.

The malt used was made from Wapana barley as follows:
The barley was cleaned in a conventional grain cleaning plant and washed until the rinse water was clear. The washed barley was covered with a solution of 0.03% Ca(OH)$_2$ and steeped with constant aeration at 13° C. After 6–8 hours the alkaline steep liquor was discarded and the barley washed in fresh water until the rinse water was clear. The seeds were covered with distilled tap water and the steep was continued at 13° C. under constant aeration for 24 hours from the start of the alkaline steep. The seeds were washed and again covered with distilled tap water. The steep was continued at 13° C. with aeration until chitting (emergence of the rootlets and beginning of acrospire growth) occurred in about 70% to 80% of the seeds. This occurred at 44 to 48 hours after the beginning of the alkaline steep. The seeds were drained, washed and placed in the germination chamber on screen shelves at a depth of about 1". The temperature of the germination chamber was held at 15° C. under a constant flow of water-saturated air. After 4 days in the chamber the green barley malt was removed and frozen. The moisture content of the malted barley was about 52–54 wt%. The malt extract was prepared by homogenizing the malt with water in a Waring blender, centrifuging the mixture and re-extracting the precipitate twice more. A typical analysis of the extract showed an activity of 900 μmoles maltose released per min. per g. malt.

For pasting and hydrolysis, the three starch fractions were combined and water was added to give approximately 30% starch solids. Green malt extract was added for liquefaction and the slurry was heated with stirring to 75° C. to paste the starch, held 10 minutes then cooled to 40° C. A second extract of green malt was added and the slurry was stirred 2–4 hours after which the temperature was raised to 60° C. In order to essentially remove all the protein with the Bird centrifuge it was necessary to dilute the slurry 1:1 with water. Initial runs were made on 30% syrup but extreme care was necessary to get proper viscosity before centrifuging. This dilution step was used because the pilot plant runs were made with inexperienced help. However, this would not be done in a commercial plant. This centrifuge step was carried out either 4 to 6 hours after the second malt addition or about 36 hours after the second malt addition (in the case of runs scheduled on the weekends).

The crude protein thus obtained was resuspended in water and again centrifuged to wash out the sugars. The crude protein fraction included 45–50% soluble sugars. The wash step removed about 80% of the sugars. The washed protein was lyophilized in the VirTis Sublimator.

For syrup production the supernatant from protein centrifugation was returned to the kettle and stirred 18 to 48 hours. The sugar composition of the syrup changed very little after the protein was removed. However, the syrup contained residual protein that could not be removed by filtration or centrifugation until the digestion had been carried out longer. After the digestion period the syrup was centrifuged by the Bird centrifuge and passed through a T. Shriver & Co. plate-and-frame press using Hyflo Super-Cel as a filter aid. The syrup was clear but yellow and contained 2 to 7 mg. protein per ml. syrup.

The syrup was decolorized by batch treatment with NAP Pulverized carbon from Calgon Corporation. To obtain a water-white product it was necessary to treat the syrup twice by stirring for 2 hours at 75° C. with 1½% carbon (based on syrup solids) and filtering it through the plate-and-frame press using Standard Super-Cel as a filtration aid. The syrup then contained about 0.25 mg protein/ml syrup. Because the syrup also contained an unacceptable amount of copper arising from the house water, it was necessary to treat it with Amberlite MB-3 (Rohm & Haas) using 1 lb. resin per 5 gal. syrup. In addition to copper removal, the ion exchange resin lowered the protein level of the unconcentrated syrup to 0.1 mg/ml.

Results

The analytical results of these pilot runs are presented hereinafter. The barleys used in this series of experiments are given in Table I. Their names describe the type and origin. The prefix "Wa" indicates a waxy barley, "sho" means a short-awned barley, and "nu" means a nude barley (i.e., one lacking a covering on the seed). The suffix denotes the parent barley: "pana" from Compana, "bet" from Betzes and "tan" from Titan.

TABLE I

Barleys Used for Pilot Plant Runs

| Barley | Treatment | Run Nos. |
|---|---|---|
| Washonupana WNB-77 | Miag-milled flour | 3,4,5,6,7,8,9 |
| Washonupana WNB-77 | Hammermilled to pass thru 1/10 screen | 1 |
| Washonupana WNB-77 | Hammermilled to pass thru 1/16 and 1/32 screens | 2,10 |
| Washonupana B-79, Inc. #2 | Hammermilled to pass thru 1/16 and 1/32 screens | 11,12,13,14 |
| Washonupana B-79, Inc. #1 | Hammermilled to pass thru 1/16 and 1/32 screens | 15,16,17,18 |
| Wapana B-79, Inc. #4 | Hammermilled to pass thru 1/16 and 1/32 screens | 19,20,21,22 |
| Wabet B-79, Inc. #7 | Hammermilled to pass thru 1/16 and 1/32 screens | 23,24,25,34 |
| Wanutan B-79, Inc. #5 | Hammermilled to pass thru 1/16 and 1/32 screens | 26,27,28,29,41 |
| Wanupana B-79, Inc. #3 | Hammermilled to pass thru 1/16 and 1/32 screens | 30,31,32,33 |
| Watan B-79, Inc. #6 | Hammermilled to pass thru 1/16 and 1/32 screens | 35,36,37 |
| Wanubet B-80, Inc. BC | Hammermilled to pass thru 1/16 and 1/32 screens | 38,39,40 |

Solids Content of Fractions

The average solids content of the various fractions are shown in Table II. The differences among values obtained for individual fractions are not large, that is, the first starch fraction was always about 41% solids, the second about 37% solids, and the third about 35%, etc.

TABLE II

Average Solids Content of Fractions Generated in Syrup Production

| Barley | % solids | | | | | | | | | | |
|---|---|---|---|---|---|---|---|---|---|---|---|
| | 1st starch | 2nd starch | 3rd starch | comb. starch | screen residue | mill water | crude protein | washed protein | protein wash liq. | syrup after protein removal | syrup after Celite treatment |
| Washonupana WNB-77* | 42.2 | 36.9 | 35.6 | 36.1 | 17.8 | 6.7 | 40.3 | 31.7 | 7.2 | 30.1 | |
| Washonupana WNB-77** | 42.6 | | 34.7 | 37.1 | 21.0 | 5.6 | 41.5 | 28.6 | 5.8 | 32.0 | |
| Washonupana WNB-77 | 41.6 | 38.3 | 35.0 | 34.2 | 19.9 | 9.7 | 41.8 | 33.9 | 6.3 | 32.8 | |
| Washonupana B-79, Inc. #2 | 41.1 | 37.9 | 37.0 | 36.8 | 19.7 | 5.7 | 38.6 | 29.9 | 6.0 | 25.7*** | |
| Washonupana B-79, Inc. #1 | 40.4 | 37.1 | 36.7 | 35.2 | 19.6 | 6.1 | 37.1 | 28.7 | 5.0 | 24.6*** | |
| Wapana B-79, Inc. #4 | 42.6 | 39.4 | 39.3 | 37.1 | 22.4 | 4.5 | 38.4 | 30.8 | 3.2 | 18.8*** | 13.8 |
| Wabet B-79, Inc. #7 | 40.3 | 36.6 | 34.8 | 37.6 | 19.6 | 5.5 | 36.0 | 28.0 | 3.7 | 20.9*** | 23.1 |
| Wanutan B-79, Inc. #5 | 39.9 | 36.8 | 33.2 | 38.5 | 22.3 | 4.6 | 35.6 | 25.8 | 3.5 | 21.2*** | 17.4 |
| Wanupana B-79, Inc. #3 | 40.7 | 36.9 | 34.5 | 40.9 | 20.7 | 5.5 | 38.5 | 30.4 | 3.2 | 19.1*** | 17.9 |
| Watan B-79, Inc. #6 | 38.6 | 36.5 | 33.1 | 35.8 | 22.7 | 4.7 | 34.7 | 27.6 | 3.8 | 20.9*** | 17.2 |
| Wanubet B-80, Inc. #BC | 36.9 | 36.8 | 33.7 | 33.2 | 18.4 | 5.3 | 39.0 | 33.8 | 3.9 | 21.6*** | 19.4 |
| Average | 40.9 | 37.3 | 35.2 | 36.6 | 20.4 | 5.8 | 38.3 | 29.9 | 4.7 | 24.3 | 18.1 |

All samples were hammermilled to pass through 1/16" and 1/32" screens except as noted.
*Miag milled
**Hammermilled through 1/16" screen
***These lower sugar concentrations were the result of diluting the syrup to more completely remove the protein in the Bird centrifuge. With an adequate centrifuge we believe this dilution would be unnecessary.

Compositional Analysis

The analyses for the barleys used for the pilot plant runs are presented in Table III. It should be noted that crude fiber does not give a full picture of dietary fiber. The material not accounted for is probably β-glucans and hemi-cellulose, etc.

TABLE III

Analysis of Barleys Used in Pilot Plant

| | % starch | % sol. sugar | % protein | % ash | % crude fiber | % Et₂O Ext. | Dry wt. lbs./ 100 lbs. barley |
|---|---|---|---|---|---|---|---|
| Washonupana WNB-77* | 51.7 | 11.6 | 17.0 | 2.1 | 0.6 | 2.2 | 92.5 |
| Washonupana WNB-77** | 52.5 | 5.7 | 17.1 | 2.7 | 1.3 | 2.1 | 91.7 |
| Washonupana WNB-77 | 49.6 | 8.0 | 17.4 | 2.5 | 1.3 | 2.6 | 92.6 |
| Washonupana B-79, Inc. #2 | 50.9 | 6.1 | 16.3 | 2.5 | 2.7 | 2.2 | 92.0 |
| Washonupana B-79, Inc. #1 | 53.2 | 6.6 | 15.4 | 1.9 | 1.4 | 2.1 | 91.6 |
| Wapana B-74, Inc. #1 | 48.6 | 6.2 | 15.6 | 2.7 | 4.5 | 2.6 | 93.0 |
| Wabet B-79, Inc. #7 | 49.0 | 5.7 | 15.0 | 2.6 | 3.3 | 2.7 | 92.9 |
| Wanutan B-79, Inc. #5 | 50.3 | 6.0 | 14.9 | 2.6 | 3.0 | 2.4 | 92.0 |
| Wanupana B-79, Inc. #3 | 51.8 | 6.3 | 16.3 | 2.3 | 1.3 | 2.4 | 91.8 |
| Watana B-79, Inc. #6 | 43.7 | 7.5 | 14.2 | 2.8 | 5.0 | 2.4 | 90.4 |

TABLE III-continued

| | Analysis of Barleys Used in Pilot Plant | | | | | | |
|---|---|---|---|---|---|---|---|
| | starch | % sol. sugar | protein | ash | % crude fiber | % Et$_2$O Ext. | Dry wt. lbs./ 100 lbs. barley |
| Wanubet B-80, Inc. #BC | 48.5 | 7.2 | 16.0 | 1.9 | 2.7 | 1.5 | 89.2 |

Values are calculated on dry basis
*Miag milled
**Hammermilled through 1/16" screen
All other barleys were hammermilled through 1/16" and 1/32" screens

Milling

The barley used in earlier pilot plant runs was Washonupana WNB-79 milled on a Miag mill at Washington State University. The bran fraction (13.4%) was removed and the remaining fractions were recombined and used as crude flour. The bran fraction included some starch which was therefore lost for syrup production.

Attempts were made to remove the bran by using the Allis mill at Montana State University, but it was not possible to separate the bran from the starch efficiently. Therefore, the grain was hammermilled and the ground whole barley was used in the process. Table IV presents the sieve analyses of Washonupana WNB-77 barley (1) milled on the Miag mill, (2) hammermilled to pass through 1/6" and 1/32" screens.

The barley hammermilled to pass through the 1/16" screen was too coarse to process well, so the barley was hammermilled to pass through both the 1/16" and 1/32" screens.

Using the whole ground barley rather than flour resulted in the increase of saccharide (starch+sugars) fractions from 38 lbs/100 lbs flour to 44.0 lbs/100 lbs using Washonupana WNB barley (Table VII).

TABLE IV

| | Sieve Analysis of Milled Barley | | | | | | |
|---|---|---|---|---|---|---|---|
| U.S. Standard Sieves Opening Diameter, mm | on 10 mesh 2.00 | on 20 mesh 0.850 | on 40 mesh 0.420 | on 60 mesh 0.250 | on 80 mesh 0.177 | on 100 mesh 0.149 | through 100 mesh 0.149 |
| Miag-milled flour | 0% | 0% | 2.9% | 27.6% | 17.9% | 3.0% | 48.2% |
| Barley Hammermilled thru 1/16" screen | 1.9 | 52.1 | 21.7 | 6.9 | 3.2 | 0.4 | 12.6 |
| Barley Hammermilled thru 1/16" and 1/32" screens | 0 | 7.0 | 18.4 | 15.5 | 33.9 | 17.5 | 6.4 |

Re-Use of Mill Water

One pilot plant run (14) was carried out to study the effects of reusing the mill water (supernatant after starch was centrifuged out). Three 50 lb batches of ground Washonupana B-79, Inc. #2 barley were milled with 200 lbs. water. Each successive batch used the mill water of the previous batch with additional water added as needed. The starches were then combined and liquefaction and saccharification carried out in the usual way. The bran protein fraction and the mill water were combined and mashed. Table V shows the analytical results.

As expected, the solids build up in the mill water. Because the Cereflo has time to continue acting on the starch, the percent of soluble sugars increases while the percent starch drops in the bran protein fraction. The pH of the bran protein fraction dropped from 6.0 for the first batch, 5.3 for the second, and to 4.8 for the third batch. If the mill water is reused in a plant operation it would probably be necessary to pasteurize it between batches.

Table V shows the results of this experiment.

TABLE V

| | Results of Re-use of Mill Water | | | | | | |
|---|---|---|---|---|---|---|---|
| | % solids | % starch a.i.[1] | d.b.[2] | % sol. sugar a.i.[1] | d.b.[2] | yield[2] (lbs) | Dry Wt. lbs/100 lbs barley |
| First Starch Fraction, 1st batch | 43.0 | 32.2 | 74.9 | 1.6 | 3.7 | 17.0 | 11.3 |
| First Starch Fraction, 2nd batch | 42.5 | 29.6 | 69.4 | 3.4 | 8.0 | 18.1 | 12.1 |
| First Starch Fraction, 3rd batch | 41.5 | 25.0 | 60.2 | 4.1 | 9.9 | 15.6 | 10.4 |
| Second Starch Fraction, 1st batch | 36.4 | 24.0 | 65.9 | 1.7 | 4.7 | 5.8 | 3.9 |
| Second Starch Fraction, 2nd batch | 38.4 | 25.7 | 66.9 | 3.9 | 10.2 | 5.4 | 3.6 |
| Second Starch Fraction, 3rd batch | 40.2 | 23.1 | 57.5 | 4.3 | 10.7 | 8.0 | 5.3 |
| Third Starch Fraction, 1st batch | 35.9 | 21.6 | 60.2 | 2.0 | 5.6 | 2.5 | 1.7 |
| Third Starch Fraction, 2nd batch | 42.1 | 22.2 | 52.7 | 4.4 | 10.5 | 2.5 | 1.7 |
| Third Starch Fraction 3rd batch | 40.3 | 24.1 | 59.8 | 4.9 | 12.2 | 3.6 | 2.4 |
| | | | | | | | 52.4 |
| Bran Protein Fraction, 1st batch | 20.3 | 5.9 | 29.1 | 1.8 | 8.9 | 10.9 | 7.3 |
| Bran Protein Fraction, 2nd batch | 20.9 | 4.8 | 23.0 | 3.9 | 18.7 | 12.6 | 8.4 |
| Bran Protein Fraction, 3rd batch | 21.6 | 4.7 | 21.8 | 4.6 | 21.3 | 12.1 | 8.1 |
| Mill Water, 1st batch | 5.4 | 1.1 | 20 | 1.7 | 31 | 7.2 | 4.8 |
| Mill Water, 2nd batch | 10.4 | 1.4 | 13 | 4.7 | 45 | 11.3 | 7.5 |
| Mill Water, 3rd batch | 12.0 | 1.3 | 11 | 5.5 | 46 | 13.9 | 9.3 |

TABLE V-continued

Results of Re-use of Mill Water

| % solids | % starch a.i.[1] | % starch d.b.[2] | % sol. sugar a.i.[1] | % sol. sugar d.b.[2] | yield[2] (lbs) | Dry Wt. lbs/100 lbs barley |
|---|---|---|---|---|---|---|
| | | | | | | 45.4 |

[1] as is
[2] dry basis

Protein Removal

In this process the starch fraction (which includes the insoluble protein) was heated to 75° C. with an extract of green malt, held 10 min., cooled to 40° C. and treated with additional malt extract and stirred for 2 to 4 hours. At this point, one of two alternative treatments was used. Either the temperature was raised to 60° C. and the syrup was stirred 45 to 48 hours, after which the protein was centrifuged out and the syrup was clarified by addition of Hyflo Super-Cel and passage through the plate-and-frame press; or, the temperature was raised to 60° C. and the bulk of the protein centrifuged out at this time (about 4 hrs. after second malt addition). However, a certain amount of protein was still bound at this point and it was necessary to stir the syrup at least another 12 hrs. at 60° C. The syrup was then clarified and the residual protein removed by addition of Hyflo Super-Cel to the syrup and passage through the plate-and-frame press. Pilot runs 6, 14, 18, 22 and 25 used the ≅48 hr. digestion time and run 10 was allowed to digest 63 hours before protein removal. For the other runs most of the protein was removed after 4 to 6 hrs. The protein analysis was essentially the same whether it remained with the syrup 48 hours or was removed after 4 hours.

The usual procedure in this series of runs was to add an extract of 0.5% green malt (based on starch) to the starch slurry for liquefaction as the starch pasted and an extract of 1% green malt for saccharification after the pasted starch was cooled to 40° C. The starch was then stirred two hours at 40° C., heated to 60° C. and stirred for the remaining time. There was very little change after 2 hours of stirring and the maltose level reached only 51.9% after 8 hours.

In Run 33, 0.1% Tenase (a bacterial α-amylase) was used for saccharification instead of 0.5% green malt extract. This gave no improvement in maltose content. In Run 34, 1% green malt extract was used for liquefaction and 0.5% green malt extract for saccharification. The maltose level of this syrup was lower.

Examination of the syrups disclosed that they had unacceptable levels of copper. This came from the water supply. Copper is known to be inhibitory to amylases. Run 41 was carried out using distilled water in every step. The maltose content of the syrup increased appreciably. The time of saccharification was short (16 hours) and, although this time was adequate for previous runs, it may be that a longer time would give a higher level of maltose in the absence of the enzyme inhibitor.

TABLE VI

Composition of Syrups

| Pilot Run | Barley Variety | % glucose | % maltose | % Maltotriose | % highers | Time of Saccharification |
|---|---|---|---|---|---|---|
| 18 | Washonupana B-79, Inc. #1 | 5.95 | 52.2 | 6.55 | 36.3 | 48 hrs. |
| 22 | Wapana B-79, Inc. #4 | 5.17 | 56.1 | 5.55 | 33.2 | 3 + cooler time |
| 25 | Wanutan B-79, Inc. #5 | 2.22 | 55.9 | 5.54 | 36.3 | 48 |
| 28 | Wabet B-79, Inc. #5 | 3.53 | 55.9 | 6.22 | 34.3 | 48 |
| 31 | Wanupana B-79, Inc. #3 | 2.19 | 56.5 | 5.47 | 35.8 | 24 |
| 33* | Wanupana B-79, Inc. #3 | 3.31 | 56.1 | 7.46 | 33.1 | 24 |
| 34** | Wabet B-79, Inc. #7 | 4.01 | 52.3 | 8.31 | 35.4 | 16 |
| 49 | Wanubet B-80, Inc. BC | 3.20 | 55.1 | 6.96 | 34.7 | 16 |
| 41*** | Wanutan B-79 | 2.66 | 59.0 | 6.77 | 31.5 | 16 |

*0.1% Tenase used for liquefaction and 1.5% green malt used for saccharification.
**1.5% green malt used for liquefaction and 0.5% green malt used for saccharification.
***Distilled water used throughout
On all other runs 0.5% green malt was used for liquefaction and 1% green malt was used for saccharification.

Conditions for Saccharification

Table VI gives the compositions of the syrups from several runs. The composition changed very little after 15 hrs. However, the maltose level is lower than expected, based on previous experiments made in the laboratory where maltose levels of about 65% were obtained.

Effects of Using Different Barley Varieties

The average yields and composition of the starch fractions obtained from different barleys are presented in Table VII. The values given are averages obtained in three or more runs except for Washonupana WNB-77 hammermilled to pass through a 1/16" screen, and the same barley hammermilled to pass through 1/16" then 1/32" screens. The first was used for one pilot run and the second for two runs.

TABLE VII

Average Yield and Composition of Starch Fractions from Various Barleys

| Barley Variety | % starch | Saccharides % sol. sugar | % starch + sugar | Dry Wt lbs/100 lbs barley | Saccharides lbs/100 lbs barley |
|---|---|---|---|---|---|
| Washonupana WNB-77* | 62.9 | 9.7 | 72.6 | 53.3 | 38.0 |
| Washonupana WNB-77** | 68.2 | 8.4 | 76.6 | 55.9 | 42.8 |

TABLE VII-continued

Average Yield and Composition of Starch Fractions from Various Barleys

| Barley Variety | % starch | Saccharides % sol. sugar | % starch + sugar | Dry Wt lbs/100 lbs barley | Saccharides lbs/100 lbs barley |
|---|---|---|---|---|---|
| Washonupana WNB-77 | 66.3 | 11.5 | 77.8 | 56.5 | 44.0 |
| Washonupana B-79 Inc. #2 | 59.6 | 10.2 | 69.8 | 49.4 | 34.5 |
| Washonupana B-79 Inc. #1 | 59.7 | 11.9 | 71.6 | 50.0 | 35.8 |
| Wapana B-79 Inc. #4 | 62.7 | 7.2 | 69.9 | 53.2 | 37.2 |
| Wabet B-79 Inc. #7 | 68.6 | 3.4 | 72.0 | 52.0 | 37.4 |
| Wanutan B-79 Inc. #5 | 66.9 | 4.6 | 71.5 | 55.7 | 39.8 |
| Wanupana B-79 Inc. #3 | 75.5 | 4.1 | 79.6 | 57.1 | 45.3 |
| Watan B-79 Inc. #6 | 72.4 | 6.7 | 79.1 | 50.7 | 40.1 |
| Wanubet B-80 Inc. #BC | 71.6 | 5.0 | 76.6 | 52.9 | 40.5 |

*Miag Milled
**Hammermilled thru 1/16" screen
All other barleys were hammermilled to pass thru 1/16" then 1/32" screen The average yield and composition of the bran protein fractions are given in Table VIII. The values for yield, % starch and % soluble sugar are averages of all the runs for each barley variety but the other analyses were on single runs, except for Wanutan (3 runs analyzed). The yields of bran protein are higher, of course, for the covered varieties (Watan, Wabet and Wapana). Wanubet also gives a high yield of bran protein.

TABLE VIII

Average Yield and Composition of Unmashed Bran Protein Fractions From Various Barleys

| Barley Variety | % starch | % sol. sugar | % protein | % ash | % crude fiber | % Et$_2$O Ext | Dry Wt lbs/100 lbs barley |
|---|---|---|---|---|---|---|---|
| Washonupana WNB-77* | 16.4 | 15.7 | | | | | 13.6 |
| Washonupana WNB-77** | 20.0 | 15.2 | | | | | 18.0 |
| Washonupana WNB-77 | 25.9 | 12.5 | | | | | 19.4 |
| Washonupana B-79 Inc. #2 | 27.4 | 9.6 | | | | | 20.6 |
| Washonupana B-79 Inc. #1 | 31.2 | 13.0 | | | | | 21.2 |
| Wapana B-79 Inc #4 | 18.5 | 8.4 | | | | | 23.6 |
| Wabet B-79 Inc #7 | 19.4 | 7.9 | 14.7 | 4.3 | 11.3 | 1.9 | 24.1 |
| Wanutan B-79 Inc. #5 | 20.9 | 6.8 | 14.6 | 4.6 | 14.8 | 1.5 | 20.6 |
| Wanupana B-79 Inc #3 | 30.6 | 8.9 | 16.9 | 4.2 | 10.6 | 2.3 | 18.5 |
| Watan B-79 Inc #6 | 22.6 | 6.7 | 11.6 | 5.7 | 20.0 | 1.5 | 26.8 |
| Wanubet B-80 Inc #BC | 33.0 | 6.0 | 15.6 | 3.2 | 7.5 | 1.4 | 24.2 |

*Miag-milled
**Hammermilled to pass through 1/16" screen
All other barleys were hammermilled to pass through 1/16" and 1/32" screens Table IX summarizes the yields and analytical results obtained with the washed proteins. Wanupana and Wanubet yield the highest % protein in the product, and Wanupana has one of the better protein yields. Wanubet is high in β-glucans and was difficult to screen in separating the bran protein fraction. The bran protein fraction yield is higher than obtained for any other nude barley because of poor separation.

TABLE IX

Average Yield and Composition of Washed Protein Fractions from Various Barleys

| Barley Variety | % sol. sugars | % protein | % ash | % crude fiber | % Et$_2$O extractable | Dry Wt lbs/100 lbs barley |
|---|---|---|---|---|---|---|
| Washonupana WNB-77* | 10.1 | 66.8 | 0.8 | 0.8 | 6.8 | 9.0 |
| Washonupana WNB-77** | 11.9 | | | | | 8.1 |
| Washonupana WNB-77 | 10.8 | 55.1 | 0.7 | 0.3 | 6.5 | 9.3 |
| Washonupana B-79 Inc. #2 | 10.8 | 64.6 | 1.1 | 3.0 | 6.3 | 11.0 |
| Washonupana B-79 Inc. #1 | 10.1 | 62.2 | 0.7 | 1.9 | 7.3 | 9.3 |
| Wapana B-79 Inc. #4 | 4.5 | | | | | 11.8 |
| Wabet B-79 Inc. #7 | 5.4 | 55.0 | 1.4 | 4.9 | 5.0 | 10.7 |
| Wanutan B-79 Inc. #5 | 7.9 | 60.0 | 1.4 | 4.1 | 5.9 | 10.2 |
| Wanupana B-79 Inc #3 | 5.5 | 66.4 | 1.4 | 3.2 | 5.3 | 10.8 |
| Watan B-79 Inc. #6 | 13.6 | 49.1 | 1.6 | 6.4 | 6.7 | 7.8 |
| Wanubet B-79 Inc. #BC | 5.7 | 67.1 | 0.9 | 3.1 | 5.2 | 9.0 |

*Miag Milled
**Hammermilled to pass thru 1/16" screen
All other barleys were hammermilled to pass thru 1/16" and 1/32" screens The washed protein from Table IX contained from 5.0 to 7.3% ether extractables which are primarily barley oil. The average composition from eight varieties gave the following distribution of fatty acids:
Palmitic: 28.9%;
Stearic: 1.6%;
Oleic: 14.6%;
Linoleic: 48.7%;
Linolenic: 4.3%;
Others: 1.9%.
This is essentially the same composition as that found in corn or wheat germ oil. Although there were no actual values reported for Vitamin E in barley oil, there are comments in the nutrition literature that barley has approximately ⅓ of the vitamin E found in wheat germ oil. This suggests the value of barley oil to be somewhere between that of corn oil and wheat germ oil which would make this oil a very valuable by-product.

Since the presence of any unsaturated vegetable oil in the protein leads to instability which results in the development of rancidity, it is proposed to extract these protein fractions with ethanol or equivalent extractant. This process will stabilize the protein, improve color and flavor, increase the protein content and greatly enhance the ease of drying thus eliminating very costly drying equipment. Since the syrup process concentrates the oil in the protein fractions, it makes the extraction of the oil more economical than would be otherwise possible.

The pasting characteristics of twelve different barley varieties were determined by the Brabender Visco-Amylograph. This technique shows promise in predicting the ease of handling of the barley variety. For example, all of the Betzes derivative varieties become much more viscous on pasting than do the Compana varieities which in turn give higher viscosities than the Titans. It also appears that additions of nude and/or short awn genes cause increases in pasting viscosities. It was further found in other work that a negative relationship exists between Brabender viscosity and α-amylase (from sprouting grain, for example) and a positive relationship exists between Brabender viscosity and β-glucan content. Barley meal that is high in β-glucan gives a "slimy" slurry when mixed with water and the slurry is difficult to screen to separate starch and bran protein fractions.

Lipids in the Barley

From Table III, it will be seen that the ether extractable material in the barleys varies from 1.5% to 2.7%. It is known, however, that ether does not extract all the lipid from barley so the actual level is higher. The major portion of the lipid material concentrates in the protein fraction (Table IV). The composition of this lipid material has not been studied, but can be postulated from earlier studies. If the protein fraction is allowed to stand at room temperature for several weeks rancidity develops, indicating that unsaturated fatty acids are present. The problems can be solved in one of two ways. An antioxident could be added to the protein fraction or the lipid material could be extracted from the protein.

This could be done with hexane or with ethanol. The latter would probably be preferable as it would be available in the plant. The alcohol could be evaporated off and recovered, leaving a "barley lipid" equal to 1% to 2% of the starting weight of barley.

Mill Water and Protein Wash Liquor

Table X summarizes the yield and soluble carbohydrates content of the mill water and the water used to wash the sugars out of the protein fraction. The values given are averages of the runs for each barley variety. It was presumed that these liquids will be used for alcohol fermentation.

TABLE X

Average Yield and Composition of Waters From the Barley Syrup Process

| | Mill Water | | Protein Wash Liquor | | Combined dry carbohydrate lbs/100 lbs barley |
|---|---|---|---|---|---|
| | % carbohydrates | Dry Wt lbs/100 lbs barley | % sol. carbohydrates | Dry Wt lbs/100 lbs barley | |
| Washonupana WNB-77* | 57 | 24.8 | 79 | 7.9 | 20.3 |
| Washonupana WNB-77** | 70 | 13.1 | 97 | 6.4 | 15.3 |
| Washonupana WNB-77 | 64 | 18.9 | 82 | 9.3 | 19.8 |
| Washonupana B-79, Inc #2 | 51 | 14.8 | 88 | 6.5 | 13.4 |
| Washonupana B-79, Inc #1 | 50 | 16.8 | 91 | 6.6 | 14.4 |
| Wapana B-79, Inc #4 | 54 | 12.0 | 78 | 4.8 | 10.2 |
| Wabet B-79, Inc #7 | 48 | 13.6 | 70 | 6.2 | 10.9 |
| Wanutan B-79, Inc #5 | 49 | 12.4 | 75 | 6.0 | 10.6 |
| Wanupana B-79, Inc #3 | 56 | 15.5 | 94 | 5.6 | 13.9 |
| Watan B-79, Inc #6 | 50 | 11.8 | 88 | 4.7 | 10.0 |
| Wanubet B-80, Inc #BC | 40 | 13.2 | 86 | 4.1 | 8.8 |

*Miag milled
**Hammermilled to pass through 1/16" screen
All other barleys were hammermilled to pass through 1/16" and 1/32" screens In this series of 41 pilot plant experiments, a total of 4300 pounds of barley was processed and about 200 lbs of barley protein was prepared. Unexpectedly, it was found that this protein contains 5–7% ether extractables. Ordinarily the lipid should be removed by alcohol extraction or an antioxidant should be added to prevent rancidity. Most of the bran protein fraction produced had to be discarded as there was not enough oven capacity to dry it all.

Approximately 250 gallons of syrup with a solids content of 15–20% were obtained. Removal of traces of residual protein from the syrup was found to be a problem and it was necessary to treat the syrup with carbon. Copper and perhaps other metals were present as impurities from the water used. These added some color and undesirable flavor to the syrup and were removed by treatment with Amberlite MB-3. The ion exchange resin also pulled out some remaining protein. After the carbon and Amberlite treatments the syrup is clear, colorless and has no off-flavor. Portions of the syrup were evaporated in an evaporator to provide 22 gallons of syrup concentrated to 70% solids or greater. A typical sugar profile of the concentrated syrup is: 3.1% glucose, 58.2% maltose, 7.0% maltotriose and 31.6% highers. The pH is 4.76 and the syrup contains approximately 0.5 mg protein/g.

Seven different varieties of barley were used, and three different crops of Washonupana. The data gathered on products from these varieties will, when considered with agronomic characteristics, help in deciding on which varieties will be suitable for the larger plants.

The following tables set forth the analytical results of these pilot plant experiments which are identified as R-1 through R-41.

| | | % sol. sugar | % protein | % ash | % crude fiber | % Et₂O Ext. | Dry wt. 100 lbs barley |
|---|---|---|---|---|---|---|---|
| | % starch | | | | | | |
| R-1 Washonupana WNB-77 | | | | | | | |
| Starch fraction #1 | 64.3 | 5.6 | | | | | 39.6 |
| Starch fraction #2 | — | — | | | | | — |
| Starch fraction #3 | 59.1 | 9.5 | | | | | 4.8 |
| Combined starches | 68.2 | 8.4 | | | | | 55.9 |
| Bran protein fraction | 20.0 | 15.2 | | | | | 18.0 |
| Final mill water | 1.8 | 67.9 | | | | | 13.1 |
| Crude protein | | 40.5 | | | | | 14.7 |
| Washed protein | | 11.9 | | | | | 8.1 |
| Protein wash liquor | | 96.6 | | | | | 6.4 |
| R-2 Washonupana WNB-77 | | | | | | | |
| Starch fraction #1 | 72.3 | 5.6 | | | | | 42.5 |
| Starch fraction #2 | 72.2 | 6.8 | | | | | 10.8 |
| Starch fraction #3 | 55.0 | 8.5 | | | | | 6.7 |
| Combined starches | | | | | | | 59.3 |
| Bran protein fraction | 23.7 | 9.8 | | | | | 16.6 |
| Final mill water | | 17.7 | | | | | |
| Crude protein | | 49.2 | | | | | 14.9 |
| Washed protein | | 5.7 | 46.9 | | 0.12 | 6.5 | 8.0 |
| Protein wash liquor | | | | | | | 8.0 |
| Syrup after protein centrifugation | | | | | | | 43.9 |
| R-3 Washonupana WNB-77 | | | | | | | |
| Starch fraction #1 | 57.0 | 6.1 | | | | | 32.0 |
| Starch fraction #2 | 79.4 | 6.4 | | | | | 8.1 |
| Starch fraction #3 | 68.6 | 6.7 | | | | | 5.1 |
| Combined starches | | | | | | | 44.7 |
| Bran protein fraction | 18.7 | 14.0 | | | | | 12.5 |
| Final mill water | 13.8 | 44.6 | | | | | 33.1 |
| Crude protein | | 43.9 | | | | | 11.2 |
| Washed protein | | 6.5 | 71.3 | 0.8 | 0.8 | 6.3 | 6.0 |
| Protein wash liquor | | 80.0 | | | | | 6.0 |
| Syrup after Protein Centrifugation | | | | | | | 33.1 |
| R-4 Washonupana WNB-77 Miag milled | | | | | | | |
| Starch fraction #1 | 56.1 | 4.1 | | | | | 26.5 |
| Starch fraction #2 | 67.9 | 6.0 | | | | | 21.0 |
| Starch fraction #3 | 58.7 | 6.5 | | | | | 6.5 |
| Combined starches | | | | | | | 53.2 |
| Bran protein fraction | 16.5 | 17.1 | | | | | 14.4 |
| Final mill water | 12.9 | 41.4 | | | | | 20.0 |
| Crude protein | | | | | | | 11.9 |
| Washed protein | | | | | | | |
| Protein wash liquor | | | | | | | |
| Syrup after protein centrifugation | | | | | | | 41.7 |
| R-5 Washonupana WNB-77 Miag milled | | | | | | | |
| Starch fraction #1 | 74.6 | 6.6 | | | | | 42.9 |
| Starch fraction #2 | 59.7 | 7.9 | | | | | 11.2 |
| Starch fraction #3 | 47.6 | 10.3 | | | | | 3.3 |
| Combined starches | | | | | | | 55.3 |
| Bran protein fraction | 7.5 | 19.1 | | | | | 13.0 |
| Final mill water | 5.8 | 56.5 | | | | | 20.3 |
| Crude protein | | 41.1 | | | | | 15.0 |
| Washed protein | | 11.5 | 70.3 | 0.8 | 0.4 | 7.6 | 8.1 |
| Protein wash liquor | | 84.2 | | | | | 7.3 |
| Syrup after protein centrifugation | | | | | | | 40.3 |
| R-6 Washonupana WNB-77 Miag milled | | | | | | | |
| Starch fraction #1  a  b | 62.1 | 5.4 | | | | | 44.6 |
| Starch fraction #2  a  b | 47.7 | 7.5 | | | | | 8.6 |
| Starch fraction #3  a  b | 44.2 | 8.9 | | | | | 3.0 |
| Combined starches | | | | | | | 57.3 |
| Bran protein fraction  a  b | 11.9 | 15.5 | | | | | 10.2 |
| Final mill water  a  b | 11.6 | 47.8 | | | | | 21.4 |
| Crude protein | | 45.8 | | | | | 21.6 |
| Washed protein  1st pass  2nd pass | | 21.1 | 56.4 | 0.90 | 0.06 | 6.3 | 13.0 |
| | | | 53.3 | 0.92 | 0.05 | 8.8 | 12.5 |
| Protein wash liquor | | 65.5 | | | | | 9.2 |

|  |  | % starch | % sol. sugar | % protein | % ash | % crude fiber | % Et₂O Ext. | Dry wt. 100 lbs barley |
|---|---|---|---|---|---|---|---|---|
| Syrup after protein centrifugation |  |  |  |  |  |  |  | 35.5 |
| R-7 Washonupana WNB-77 |  |  |  |  |  |  |  |  |
| Starch fraction #1 |  | 78.8 | 5.8 |  |  |  |  | 44.8 |
| Starch fraction #2 |  | 63.4 | 7.5 |  |  |  |  | 10.0 |
| Starch fraction #3 |  | 57.8 | 8.6 |  |  |  |  | 3.1 |
| Combined starches |  | 64.9 | 8.3 |  |  |  |  | 53.5 |
| Bran protein fraction |  | 16.0 | 17.7 |  |  |  |  | 11.3 |
| Final Mill Water |  | 16.4 | 43.8 |  |  |  |  | 22.8 |
| Crude protein |  |  | 48.9 |  |  |  |  | 15.5 |
| Washed protein |  |  | 9.5 | 66.8 | 0.7 | 1.6 | 6.3 | 7.3 |
| Protein wash liquor |  |  | 84.7 |  |  |  |  | 8.0 |
| Syrup after protein centrifugation |  |  |  |  |  |  |  | 37.5 |
| Washed screen residue |  | 0.4 | 13.2 | 35.3 | 1.8 | 5.8 | 6.0 | 10.1 |
| Supernatant from mashing |  |  | 71.2 |  |  |  |  | 23.5 |
| R-8 Washonupana WNB-77 Miag milled |  |  |  |  |  |  |  |  |
| Starch fraction #1 |  | 71.5 | 5.2 |  |  |  |  | 43.3 |
| Starch fraction #2 |  | 60.9 | 5.7 |  |  |  |  | 7.6 |
| Starch fraction #3 |  | 54.2 | 7.2 |  |  |  |  | 3.3 |
| Combined starches |  | 51.5 | 11.7 |  |  |  |  | 53.2 |
| Bran Protein fraction |  | 14.9 | 16.1 |  |  |  |  | 11.5 |
| Final Mill Water |  | 14.9 | 33.9 |  |  |  |  | 22.4 |
| Crude Protein |  |  | 45.3 |  |  |  |  | 18.9 |
| Washed Protein |  |  | 13.4 | 66.0 |  |  |  | 11.2 |
| Protein wash liquor |  |  | 89.3 | 62.6 | 0.7 | 0.1 | 6.2 | 8.5 |
| Syrup after Protein centrifugation |  |  |  |  |  |  |  | 35.2 |
| Washed screen residue |  |  | 17.3 |  |  |  |  | 8.8 |
| Supernatant from mashing |  |  | 81.3 |  |  |  |  | 4.9 |
| R-9 Washonupana WNB-77 Miag milled |  |  |  |  |  |  |  |  |
| Starch fraction #1 |  | 60.2 | 4.7 |  |  |  |  | 36.4 |
| Starch fraction #2 |  | 67.9 | 5.7 |  |  |  |  | 10.4 |
| Starch fraction #3 |  | 69.9 | 6.6 |  |  |  |  | 5.3 |
| Combined starches |  | 73.3 | 9.0 |  |  |  |  | 50.4 |
| Bran protein fraction |  | 29.2 | 10.4 |  |  |  |  | 22.5 |
| Final Mill Water |  | 8.5 | 44.7 |  |  |  |  | 12.4 |
| Crude Protein |  |  | 38.6 |  |  |  |  | 8.1 |
| Washed protein |  |  | 9.8 | 59.7 | 0.8 | 0.5 | 6.9 | 12.4 |
| Protein wash liquor |  |  | 68.4 |  |  |  |  | 12.3 |
| Syrup after protein centrifugation |  |  |  |  |  |  |  | 31.3 |
| Washed screen residue |  |  |  |  |  |  |  |  |
| Supernatant from mashing |  |  |  |  |  |  |  |  |
| R-10 Washonupana WNB-77 |  |  |  |  |  |  |  |  |
| Starch fraction #1 | a | 76.4 | 6.3 |  |  |  |  | 38.3 |
|  | b | 81.5 | 8.0 |  |  |  |  |  |
| Starch fraction #2 | a | 72.2 | 7.5 |  |  |  |  | 11.3 |
|  | b | 69.8 | 9.5 |  |  |  |  |  |
| Starch fraction #3 | a | 65.5 | 5.8 |  |  |  |  | 4.7 |
|  | b | 61.6 | 12.5 |  |  |  |  |  |
| Combined starches |  | 66.3 | 14.9 |  |  |  |  | 52.1 |
| Bran Protein fraction | a | 32.1 | 13.5 |  |  |  |  | 22.1 |
|  | b | 23.9 | 16.7 |  |  |  |  |  |
| Final Mill Water | a | 11.3 | 52.8 |  |  |  |  | 18.9 |
|  | b | 9.8 | 54.3 |  |  |  |  |  |
| Crude Protein |  |  | 39.6 |  |  |  |  | 19.7 |
| Washed Protein |  |  | 15.9 | 64.0 | 0.7 | 0.4 | 6.5 | 10.6 |
| Protein wash liquor |  |  | 82.3 |  |  |  |  | 9.3 |
| Syrup after Protein centrifugation |  |  |  |  |  |  |  | 34.8 |
| Washed screen residue |  |  |  |  |  |  |  |  |
| Supernatant from mashing |  |  |  |  |  |  |  |  |
| R-11 Washonupana B-79 Inc. #2 |  |  |  |  |  |  |  |  |
| Starch fraction #1 | a | 74.5 | 3.4 |  |  |  |  | 28.8 |
|  | b | 72.8 | 3.3 |  |  |  |  |  |
| Starch fraction #2 | a | 62.4 | 3.7 |  |  |  |  | 10.6 |
|  | b | 77.1 | 3.8 |  |  |  |  |  |
| Starch fraction #3 | a | 62.2 | 4.6 |  |  |  |  | 6.7 |
|  | b | 68.9 | 4.1 |  |  |  |  |  |

-continued

| | | % starch | % sol. sugar | % protein | % ash | % crude fiber | % Et₂O Ext. | Dry wt. 100 lbs barley |
|---|---|---|---|---|---|---|---|---|
| Combined starches | | 59.1 | 10.4 | | | | | 43.3 |
| Bran Protein | a | 28.3 | 8.6 | | | | | 21.7 |
| Fraction | b | 35.6 | 9.0 | | | | | |
| Final Mill Water | a | 21.4 | 33.9 | | | | | 16.5 |
| | b | 17.2 | 23.4 | | | | | |
| Crude Protein | | | 40.4 | | | | | 16.7 |
| Washed Protein | | | 8.2 | | | | | 9.5 |
| Protein Wash Liquor | | | 102 | | | | | 6.5 |
| Syrup after Protein centrifugation | | | | | | | | 30.6 |
| R-12 Washonupana B-79 Inc. #2 | | | | | | | | |
| Starch fraction #1 | a | 60.3 | 5.2 | | | | | 33.0 |
| | b | 57.3 | 4.5 | | | | | |
| Starch fraction #2 | a | 55.4 | 5.6 | | | | | 12.5 |
| | b | 63.8 | 4.3 | | | | | |
| Starch fraction #3 | | 52.4 | 6.1 | | | | | 4.8 |
| Combined starches | | 57.5 | 10.1 | | | | | 49.6 |
| Bran protein | a | 25.0 | 9.5 | | | | | 20.2 |
| fraction | b | 25.5 | 9.6 | | | | | |
| Final mill water | a | 7.0 | 28.2 | | | | | 20.0 |
| | b | 13.2 | 30.2 | | | | | |
| Crude protein | | | 49.6 | | | | | 18.2 |
| Washed protein | | | 12.6 | 65.2 | 1.0 | 3.3 | 5.9 | 10.9 |
| Protein wash liquor | | | 79.7 | | | | | 7.6 |
| Syrup after protein centrifugation | | | | | | | | 32.5 |
| Washed screen residue | | | | 22.0 | | | | 13.9 |
| Washed masched screen residue | | | | 26.7 | | | | |
| Supernatant from mashing | | | 71.2 | | | | | 9.5 |
| Lactic acid | | | | 61.3 | 1.1 | 4.8 | 4.9 | |
| insoluble protein | | | | 60.4 | | | | |
| R-13 Washonupana B-79 Inc. #2 | | | | | | | | |
| Starch fraction #1 | a | 55.4 | 5.5 | | | | | 34.4 |
| | b | 59.8 | 4.4 | | | | | |
| Starch fraction #2 | a | 61.2 | 5.5 | | | | | 11.5 |
| | b | 61.4 | 4.8 | | | | | |
| Starch fraction #3 | a | 57.6 | 7.1 | | | | | 5.4 |
| | b | 59.8 | 5.9 | | | | | |
| Combined starches | | 60.7 | 10.1 | | | | | 53.3 |
| Bran protein | a | 21.8 | 9.3 | | | | | 20.0 |
| fraction | b | 28.1 | 11.4 | | | | | |
| Final mill water | a | 11 | 54 | | | | | 13.4 |
| | b | 14 | 39 | | | | | |
| Crude protein | | | 41.9 | | | | | 17.0 |
| Washed protein | | | 8.0 | 64.0 | 1.1 | 2.6 | 6.7 | 10.4 |
| Protein wash liquor | | | 97.3 | | | | | 4.0 |
| Syrup after protein centrifugation | | | | | | | | 35.9 |
| Washed screen residue | | | | 22.0 | | | | 14.1 |
| Supernatant from mashing | | | 64 | | | | | 17.8 |
| R-14 Washonupana B-79 Inc. #2 | | | | | | | | |
| Starch fraction #1 | a | 74.9 | 3.7 | | | | | 33.8 |
| | b | 69.4 | 8.0 | | | | | |
| | c | 60.2 | 9.9 | | | | | |
| Starch fraction #2 | a | 65.9 | 4.7 | | | | | 12.8 |
| | b | 66.9 | 10.2 | | | | | |
| | c | 57.5 | 10.7 | | | | | |
| Starch fraction #3 | a | 60.2 | 5.6 | | | | | 5.7 |
| | b | 52.7 | 10.5 | | | | | |
| | c | 59.8 | 12.2 | | | | | |
| Combined starches | | 53.9 | 13.3 | | | | | 35.8 |
| Bran protein | a | 29.1 | 8.9 | | | | | 23.7 |
| fraction | b | 23.0 | 18.7 | | | | | |
| | c | 21.8 | 21.3 | | | | | |
| Final mill water | a | 20 | 31 | | | | | 14.4 |
| | b | 13 | 45 | | | | | |
| | c | 11 | 46 | | | | | |
| Crude protein | | | 33.8 | | | | | 18.7 |
| Washed protein | | | 14.3 | | | | | 13.0 |
| Protein wash liquor | | | 73.6 | | | | | 8.0 |
| Syrup after protein centrifugation | | | | 2.7 | | | | 39.3 |

-continued

| | | % starch | % sol. sugar | % protein | % ash | % crude fiber | % Et$_2$O Ext. | Dry wt. 100 lbs barley |
|---|---|---|---|---|---|---|---|---|
| Washed screen residue | | | 16 | 21.4 | 3.1 | 11.6 | 4.2 | 13.7 |
| | | | | 22.8 | 3.0 | 8.5 | 5.5 | |
| Supernatant from mashing | | | 53 | | | | | 19.6 |
| R-15 Washonupana B-79 Inc. #1 | | | | | | | | |
| Starch fraction #1 | a | 71.3 | 3.0 | | | | | 17.8 |
| | b | 66.8 | 3.1 | | | | | |
| Starch fraction #2 | a | 69.1 | 3.0 | | | | | 16.9 |
| | b | 62.6 | 3.8 | | | | | |
| Starch fraction #3 | a | 65.3 | 5.3 | | | | | 10.6 |
| | b | 59.9 | 5.4 | | | | | |
| Combined starches | | 64.2 | 10.0 | | | | | 44.0 |
| Bran protein | a | 36.3 | 6.6 | | | | | 23.9 |
| fraction | b | 27.0 | 5.9 | | | | | |
| Final mill water | a | 14 | 16 | | | | | 16.8 |
| | b | 15 | 16 | | | | | |
| Crude protein | | | 44.1 | | | | | 14.8 |
| Washed protein | | | 9.4 | | | | | 7.9 |
| Protein wash liquor | | | 92 | | | | | 6.9 |
| Lactic acid insoluble protein | | | | | | | | 4.4 |
| Lactic acid insoluble protein wash liquor | | | | 62.7 | 0.6 | 5.2 | 4.9 | 0.7 |
| Washed screen residue | | | 20.3 | 24.4 | 2.3 | 7.3 | 5.2 | 14.0 |
| | | | | 25.4 | 2.2 | 3.8 | 9.4 | |
| Supernatant from mashing | | | 59.6 | | | | | 23.1 |
| Syrup after protein centrifugation | | | | | | | | 30.6 |
| R-16 Washonupana B-79 Inc. #1 | | | | | | | | |
| Starch fraction #1 | a | 78.5 | 5.0 | | | | | 35.1 |
| | b | 66.8 | 4.7 | | | | | |
| Starch fraction #2 | a | 61.0 | 5.1 | | | | | 9.1 |
| | b | 59.8 | 5.9 | | | | | |
| Starch fraction #3 | a | 68.6 | 4.8 | | | | | 6.6 |
| | b | 64.3 | 5.7 | | | | | |
| Combined starches | | 71.0 | 12 | | | | | 50.4 |
| Bran protein | a | 34 | 9.6 | | | | | 20.9 |
| fraction | b | 32 | 8.5 | | | | | |
| Final mill water | a | 23 | 20 | | | | | 16.9 |
| | b | 18 | 25 | | | | | |
| Crude Protein | | | 26.9 | | | | | 15.4 |
| Washed Protein | | | 8.8 | | | | | 8.6 |
| Protein wash liquor | | | 80.0 | | | | | 6.3 |
| Syrup after protein centrifugation | | | | | | | | 34.8 |
| Lactic acid soluble protein | | | | | | | | 6.4 |
| Lactic acid insoluble protein | | | | 87.6 | 0.4 | 0.0 | 0.9 | |
| R-17 Washonupana B-79 Inc. #1 | | | | | | | | |
| Starch fraction #1 | | | | | | | | 40.1 |
| Starch fraction #2 | | | | | | | | 9.8 |
| Starch fraction #3 | | | | | | | | 4.3 |
| Combined starches | | 52.8 | 12 | | | | | 53.1 |
| Bran protein | a | 28.4 | 15.8 | | | | | 19.8 |
| fractions | b | 36.8 | 17.0 | | | | | |
| Final mill water | a | 8 | 50 | | | | | 13.5 |
| | b | 4 | 63 | | | | | |
| Crude protein | | | 45.9 | | | | | 15.9 |
| Washed protein | | | 7.5 | 65.2 | 0.7 | 2.4 | 6.7 | 9.9 |
| Protein wash liquor | | | 100 | | | | | 6.5 |
| Syrup after protein centrifugation | | | | | | | | 39.4 |
| R-18 Washonupana B-79 Inc. #1 | | | | | | | | |
| Starch fraction #1 | | | | | | | | 39.9 |
| Starch fraction #2 | | | | | | | | 9.6 |
| Starch fraction #3 | | | | | | | | 4.3 |
| Combined starches | | 62.5 | 13.4 | | | | | 48.1 |
| Bran protein | a | 28.7 | 17.3 | | | | | 20.1 |
| fraction | b | 25.9 | 22.7 | | | | | |
| Final mill water | a | 6 | 58 | | | | | 20.1 |
| | b | 11 | 54 | | | | | |
| Crude protein | | | 46.8 | | | | | 17.3 |

-continued

|  | | % starch | % sol. sugar | % protein | % ash | % crude fiber | % Et$_2$O Ext. | Dry wt. 100 lbs barley |
|---|---|---|---|---|---|---|---|---|
| Washed protein | | | 14.8 | 59.1 | 0.6 | 1.3 | 7.9 | 10.9 |
| Protein wash liquor | | | 93.5 | | | | | 6.8 |
| Syrup after protein centrifugation | | | | | | | | 36.9 |
| Ashed screen residue | | | 16.7 | 22.6 | 3.5 | 9.8 | 4.5 | 13.0 |
| Supernatant from mashing | | | 79.3 | | | | | 20.1 |
| R-19 Wapana B-79, Inc. #4 | | | | | | | | |
| Starch fraction #1 | | | | | | | | 43.0 |
| Starch fraction #2 | | | | | | | | 8.6 |
| Starch fraction #3 | | | | | | | | 4.3 |
| Combined starches | | | 9.2 | | | | | 55.6 |
| Bran protein | a | 15.8 | 8.5 | | | | | 20.2 |
| fraction | b | 16.0 | 9.9 | | | | | |
| Final mill water | a | 5 | 52 | | | | | 11.3 |
| | b | 7 | 58 | | | | | |
| Crude protein | | | | 23 | | | | 17.1 |
| Washed protein | | | | 4.3 | | | | 12.1 |
| Protein wash liquor | | | | 77 | | | | 4.4 |
| Syrup after protein centrifugation | | | | | | | | 38.7 |
| Lactic acid insoluble protein | | | | 59.1 | 1.8 | 6.1 | 5.3 | 9.1 |
| Lactic acid soluble protein | | | | 44.6 | 49.3 | 0.5 | 0.7 | |
| R-20 Wapana B-79, Inc. #1 | | | | | | | | |
| Starch fraction #1 | a | 70.6 | 5.3 | | | | | 35.6 |
| | b | 72.7 | 3.8 | | | | | |
| Starch fraction #2 | a | 58.0 | 5.3 | | | | | 11.9 |
| | b | 67.1 | 4.1 | | | | | |
| Starch fraction #3 | a | 64.4 | 5.5 | | | | | 4.2 |
| | b | 49.3 | 5.0 | | | | | |
| Combined starches | | 59.7 | 7.1 | | | | | 53.2 |
| Bran protein | a | 18 | 8.6 | | | | | 24.2 |
| fraction | b | 20 | 6.7 | | | | | |
| Final mill water | a | 9 | 38 | | | | | 12.7 |
| | b | 14 | 31 | | | | | |
| Crude Protein | | | | 22.6 | | | | 16.5 |
| Washed protein | | | | 3.7 | | | | 11.4 |
| Protein wash liquor | | | | 52 | | | | 4.8 |
| Syrup after protein centrifugation | | | | | | | | 40.7 |
| R-21 Wapana B-79, Inc. #1 | | | | | | | | |
| Starch fraction #1 | | | | | | | | 44.2 |
| Starch fraction #2 | | | | | | | | 8.7 |
| Starch fraction #3 | | | | | | | | 3.8 |
| Combined starches | | 65.2 | 7.9 | | | | | 52.7 |
| Bran protein | a | 17.2 | 9.9 | | | | | 23.5 |
| fraction | b | 14.9 | 8.7 | | | | | |
| Final mill water | a | 11 | 43 | | | | | 12.5 |
| | b | 9 | 41 | | | | | |
| Crude protein | | | | 23.2 | | | | 17.1 |
| Washed protein | | | | 3.9 | | | | 12.0 |
| Protein wash liquor | | | | 90.6 | | | | 4.2 |
| Syrup after protein centrifugation | | | | | | | | 38.2 |
| Unmashed bran protein | | | | 14.7 | 5.0 | 18.7 | 1.9 | 20.6 |
| Mashed bran protein | | | 43.8 | 19.0 | 4.9 | 23.6 | 2.7 | |
| Supernatant from mashing | | | 37.9 | | | | | 17.5 |
| R-22 Wapana B-79, Inc. #4 | | | | | | | | |
| Starch fraction #1 | | | | | | | | 35.6 |
| Starch fraction #2 | | | | | | | | 10.5 |
| Starch fraction #3 | | | | | | | | 4.1 |
| Combined starches | | 70.5 | 4.5 | | | | | 49.2 |
| Bran protein fraction | | 23.1 | 7.4 | | | | | 26.3 |
| Final mill water | | 18 | 38 | | | | | 11.6 |
| Crude protein | | | | 19.7 | | | | 17.3 |
| Washed protein | | | | 6.0 | | | | 11.6 |
| Protein wash liquor | | | | 93 | | | | 5.6 |
| Syrup after protein centrifugation | | | | | | | | 33.9 |
| Celite-treated syrup | | | | 0.14 | | | | 22.9 |

-continued

| | % starch | % sol. sugar | % protein | % ash | % crude fiber | % Et$_2$O Ext. | Dry wt. 100 lbs barley |
|---|---|---|---|---|---|---|---|
| Carbon-treated syrup R-23 Wabet B-79, Inc. #7 | | | 0.067 | | | | |
| Starch fraction #1 | | | | | | | 33.9 |
| Starch fraction #2 | | | | | | | 12.5 |
| Starch fraction #3 | | | | | | | 5.1 |
| Combined starches | 64.9 | 4.5 | | | | | 51.5 |
| Bran protein fraction | 25.0 | 11.3 | | | | | 24.1 |
| Final mill water | 10 | 47 | | | | | 12.5 |
| Crude protein | | 27.0 | | | | | 17.1 |
| Washed protein | | 4.6 | | | | | 10.8 |
| Protein wash liquor | | 78.9 | | | | | 4.5 |
| Syrup after protein centrifugation | | | | | | | 35.9 |
| R-24 Wabet B-79, Inc. #7 | | | | | | | |
| Starch fraction #1 | 68.4 | 2.8 | | | | | 31.6 |
| Starch fraction #2 | 69.5 | 3.5 | | | | | 11.3 |
| Starch fraction #3 | 68.0 | 4.2 | | | | | 6.1 |
| Combined starches | 65.1 | 2.4 | | | | | 53.2 |
| Bran protein fraction | 26.0 | 7.0 | 14.7 | 4.3 | 11.3 | 1.9 | 26.7 |
| Final mill water | 20 | 23 | | | | | 13.7 |
| Crude protein | | 29.7 | | | | | 15.7 |
| Washed protein | | 2.6 | | | | | 9.9 |
| Protein wash liquor | | 59 | | | | | 6.3 |
| Syrup after protein centrifugation | | | | | | | 32.8 |
| Washed bran protein | | 9.3 | 20.5 | 4.7 | 18.9 | 2.8 | 15.5 |
| Supernatant from mashing | | 52 | | | | | 13.6 |
| Washed mashed bran protein | | | 20.4 | 4.8 | 23.2 | 1.8 | |
| Lactic acid soluble protein | | | | | | | 0.9 |
| Lactic acid insoluble protein | | | 92.1 | 0.3 | 0.1 | 0.3 | 4.5 |
| R-25 Wabet B-79, Inc. #7 | | | | | | | |
| Starch fraction #1 | 68.4 | 3.4 | | | | | 37.2 |
| Starch fraction #2 | 22.8 | 6.7 | | | | | 10.3 |
| Starch fraction #3 | 17 | 33 | | | | | 5.5 |
| Combined starches | | 25.9 | | | | | |
| Bran protein fraction | | 8.2 | 55.0 | 1.4 | 4.9 | 5.0 | 22.0 |
| Final mill water | | 53.5 | | | | | 14.0 |
| Crude protein | | | | | | | 18.1 |
| Washed protein | | | | | | | 11.5 |
| Protein wash liquor | | | | | | | 8.0 |
| Syrup after protein centrifugation | | | | | | | 32.5 |
| Celite-treated syrup | | | | | | | 27.2 |
| R-26 Wanutan B-79, Inc. #5 | | | | | | | |
| Starch fraction #1 | | | | | | | 43.7 |
| Starch fraction #2 | | | | | | | 8.8 |
| Starch fraction #3 | | | | | | | 3.7 |
| Combined starches | 57.9 | 3.7 | | | | | |
| Bran protein fraction | 23.4 | 6.5 | | | | | 19.9 |
| Final mill water | 9.3 | 41.9 | | | | | 11.6 |
| Crude protein | | 39.7 | | | | | 16.1 |
| Washed protein | | 8.1 | | | | | 11.1 |
| Protein wash liquor | | 77.4 | | | | | 6.1 |
| Syrup after protein centrifugation | | | | | | | 38.3 |
| Lactic acid soluble protein | | | 82.1 | 1.8 | 0.3 | | |
| R-27 Wanutan B-79, Inc. #5 | | | | | | | |
| Starch fraction #1 | 65.2 | 3.1 | | | | | 40.0 |
| Starch fraction #2 | | | | | | | |
| Starch fraction #3 | 68.5 | 3.9 | | | | | 3.9 |
| Combined starches | 64.9 | 2.9 | | | | | 54.1 |
| Bran protein fraction | 24.2 | 5.3 | 14.3 | 4.9 | 15.8 | 1.9 | 21.2 |

-continued

|  | % starch | % sol. sugar | % protein | % ash | % crude fiber | % Et$_2$O Ext. | Dry wt. 100 lbs barley |
|---|---|---|---|---|---|---|---|
| Final mill water | 14.9 | 19.1 |  |  |  |  | 12.3 |
| Crude protein |  | 27.3 |  |  |  |  | 15.5 |
| Washed protein |  | 7.0 |  |  |  |  | 8.8 |
| Protein wash liquor |  | 73.3 |  |  |  |  | 6.0 |
| Syrup after protein centrifugation |  |  |  |  |  |  | 39.5 |
| Mashed bran protein |  | 8.3 | 20.0 | 4.8 | 19.4 | 2.4 | 14.0 |
| Supernatant from mashing |  | 80.0 |  |  |  |  | 17.4 |
| Washed mashed bran protein |  |  | 19.3 | 5.0 | 23.6 | 1.6 |  |
| Lactic acid insoluble protein |  |  | 57.6 | 1.1 | 6.0 | 5.3 |  |
| R-28 Wanutan B-79, Inc. #5 |  |  |  |  |  |  |  |
| Starch fraction #1 |  |  |  |  |  |  | 41.2 |
| Starch fraction #2 |  |  |  |  |  |  | 9.5 |
| Starch fraction #3 |  |  |  |  |  |  | 4.1 |
| Combined starches | 70.9 | 4.5 |  |  |  |  | 53.3 |
| Bran protein fraction | 20.0 | 7.7 |  |  |  |  | 22.4 |
| Final mill water | 12.5 | 37.5 |  |  |  |  | 12.8 |
| Crude protein |  |  |  |  |  |  |  |
| Washed protein |  | 7.0 | 58.3 | 1.5 | 4.4 | 5.6 | 10.4 |
| Protein wash liquor |  | 75.0 |  |  |  |  | 6.1 |
| Syrup after protein centrifugation |  |  |  |  |  |  | 36.8 |
| Final concentrated syrup |  |  |  |  |  |  | 9.2 |
| R-29 Wanutan B-79, Inc. #5 |  |  |  |  |  |  |  |
| Starch fraction #1 |  |  |  |  |  |  | 39.7 |
| Starch fraction #2 |  |  |  |  |  |  | 11.5 |
| Starch fraction #3 |  |  |  |  |  |  | 4.0 |
| Combined starches | 70.6 | 5.2 |  |  |  |  | 60.1 |
| Bran protein a | 21.2 | 7.2 | 14.9 | 4.3 | 13.5 | 1.4 | 20.6 |
| fraction b | 15.4 | 7.5 |  |  |  |  |  |
| Final mill water a | 9.3 | 44.2 |  |  |  |  | 11.9 |
| b | 11.4 | 38.6 |  |  |  |  |  |
| Crude protein |  | 37.9 |  |  |  |  | 15.5 |
| Washed protein |  | 12.9 |  |  |  |  | 9.5 |
| Protein wash liquor |  | 39.7 |  |  |  |  | 6.6 |
| Lactic acid soluble protein |  |  | 56.9 | 1.2 | 5.8 | 7.2 | 37.5 |
| R-30 Wanupana B-79, Inc. #3 |  |  |  |  |  |  |  |
| Starch fraction #1 |  |  |  |  |  |  | 32.4 |
| Starch fraction #2 |  |  |  |  |  |  | 8.9 |
| Starch fraction #3 |  |  |  |  |  |  | 4.0 |
| Combined starches | 71.6 | 3.9 |  |  |  |  | 56.5 |
| Bran protein fraction | 31.3 | 8.9 |  |  |  |  | 17.5 |
| Final mill water | 17.6 | 35.3 |  |  |  |  | 14.5 |
| Crude protein |  | 25.9 |  |  |  |  | 16.4 |
| Washed protein |  | 4.3 | 68.7 | 1.3 | 3.2 | 4.7 | 11.6 |
| Protein wash liquor |  | 95.9 |  |  |  |  | 4.5 |
| Syrup after protein centrifugation |  |  |  |  |  |  | 37.3 |
| Celite treated syrup |  |  |  |  |  |  | 31.6 |
| R-31 Wanupana B-79, Inc. #3 |  |  |  |  |  |  |  |
| Starch fraction #1 | 75.8 | 4.4 |  |  |  |  | 44.5 |
| Starch fraction #2 | 72.0 | 5.4 |  |  |  |  | 9.5 |
| Starch fraction #3 | 57.1 | 6.8 |  |  |  |  | 4.3 |
| Combined starches | 77.4 | 4.8 |  |  |  |  | 57.7 |
| Bran protein fraction | 25.9 | 9.3 | 16.9 | 4.2 | 10.6 | 2.3 | 17.6 |
| Final mill water | 30.6 | 32.7 |  |  |  |  | 13.7 |
| Crude protein |  |  |  |  |  |  |  |
| Washed protein |  | 5.0 | 64.7 | 1.4 | 2.9 | 5.6 | 11.5 |
| Protein wash liquor |  | 96.3 |  |  |  |  | 5.7 |
| Syrup after protein centrifugation |  |  |  |  |  |  | 38 |
| Mashed bran protein |  | 12.2 | 22.8 | 4.7 | 16.8 | 3.9 | 10.8 |
| Supernatant from mashing |  | 63.5 |  |  |  |  | 20.0 |
| Washed mashed bran protein |  |  | 23.5 | 4.9 | 20.2 | 2.4 |  |

-continued

| | | % starch | % sol. sugar | % protein | % ash | % crude fiber | % Et₂O Ext. | Dry wt. 100 lbs barley |
|---|---|---|---|---|---|---|---|---|
| R-32 Wanupana B-79, Inc. #3 | | | | | | | | |
| Starch fraction #1 | | | | | | | | 26.8 |
| Starch fraction #2 | | | | | | | | 14.7 |
| Starch fraction #3 | | | | | | | | 5.7 |
| Combined starches | | 77.8 | 3.1 | | | | | 52.5 |
| Bran protein fraction | | 33.8 | 9.1 | | | | | 20.9 |
| Final mill water | | 28.8 | 24.2 | | | | | 18.9 |
| Crude protein | | | 26.2 | | | | | 11.9 |
| Washed protein | | | 3.0 | 69.8 | 1.4 | 3.6 | 4.6 | 8.8 |
| Protein wash liquor | | | 92.9 | | | | | 2.8 |
| Syrup after protein centrifugation | | | | | | | | 35.2 |
| R-33 Wanupana B-79, Inc. #7 | | | | | | | | |
| Starch fraction #1 | | | | | | | | 35.4 |
| Starch fraction #2 | | | | | | | | 11.7 |
| Starch fraction #3 | | | | | | | | 5.8 |
| Combined starches | | 75.2 | 4.4 | | | | | 61.5 |
| Bran protein | a | 32.0 | 7.4 | | | | | 17.8 |
| fraction | b | 30.4 | 9.2 | | | | | |
| Final mill water | a | 20.4 | 29.6 | | | | | 14.7 |
| | b | 10.0 | 50.0 | | | | | |
| Crude protein | | | 31.4 | | | | | 18.4 |
| Washed protein | | | 9.6 | 62.4 | 1.3 | 2.9 | 6.1 | 11.4 |
| Protein wash liquor | | | 89.1 | | | | | 6.7 |
| Syrup after protein centrifugation | | | | | | | | 40.3 |
| Celite-treated syrup | | | | | | | | 28.9 |
| R-34 Wabet B-79, Inc. #7 | | | | | | | | |
| Starch fraction #1 | | | | | | | | 34.0 |
| Starch fraction #2 | | | | | | | | 11.2 |
| Starch fraction #3 | | | | | | | | 5.4 |
| Combined starches | | 74.4 | 3.4 | | | | | 55.1 |
| Bran protein | a | 20.7 | 6.9 | | | | | 24.7 |
| fraction | b | 27.0 | 6.1 | | | | | |
| Final mill water | a | 18.9 | 30.2 | | | | | 14.3 |
| | b | 18.6 | 18.6 | | | | | |
| Crude protein | | | 34.0 | | | | | 16.4 |
| Washed protein | | | 6.2 | 54.2 | 1.6 | 5.9 | 5.8 | 10.5 |
| Protein wash liquor | | | 88.1 | | | | | 6.1 |
| Syrup after protein centrifugation | | | | | | | | 34.1 |
| Celite-treated syrup | | | | | | | | 31.7 |
| R-35 Watan B-79, Inc. #6 | | | | | | | | |
| Starch fraction #1 | | | | | | | | 35.9 |
| Starch fraction #2 | | | | | | | | 10.1 |
| Starch fraction #3 | | | | | | | | 4.0 |
| Combined starches | | 73.8 | 4.0 | | | | | 55.5 |
| Bran protein | a | 25.4 | 5.7 | | | | | 26.5 |
| fraction | b | 21.9 | 5.5 | | | | | |
| Final mill water | a | 17.0 | 31.9 | | | | | 12.7 |
| | b | 14.3 | 36.7 | | | | | |
| Crude protein | | | 28.2 | | | | | 13.4 |
| Washed protein | | | 25.2 | 48.4 | 1.5 | 5.9 | 6.9 | 8.1 |
| Protein wash liquor | | | 88.5 | | | | | 5.2 |
| Syrup after protein centrifugation | | | | | | | | 37.4 |
| Celite-treated syrup | | | | | | | | 24.7 |
| R-36 Watan B-79, Inc. #6 | | | | | | | | |
| Starch fraction #1 | a | 75.9 | 3.9 | | | | | 34.5 |
| | b | 72.3 | 3.7 | | | | | |
| Starch fraction #2 | a | 76.4 | 4.1 | | | | | 12.3 |
| | b | 72.3 | 4.7 | | | | | |
| Starch fraction #3 | a | 68.7 | 5.7 | | | | | 3.9 |
| | b | 65.5 | 5.8 | | | | | |
| Combined starches | | 71.9 | 5.1 | | | | | 52.6 |
| Bran protein | a | 20.5 | 6.7 | 11.6 | 5.7 | 20.0 | 1.5 | 24.9 |
| fraction | b | 21.5 | 6.7 | | | | | |
| Final mill water | a | 12.8 | 36.2 | | | | | 11.8 |
| | b | 14.3 | 34.7 | | | | | |
| Crude protein | | | 29.8 | | | | | 13.3 |
| Washed protein | | | 5.5 | 53.3 | 1.5 | 6.0 | 7.3 | 8.9 |

|  |  | % starch | % sol. sugar | % protein | % ash | % crude fiber | % Et$_2$O Ext. | Dry wt. 100 lbs barley |
|---|---|---|---|---|---|---|---|---|
| Protein wash liquor | | | 90.5 | | | | | 4.3 |
| Syrup after protein centrifugation | | | | | | | | 36.2 |
| Celite-treated syrup | | | | | | | | 26.3 |
| R-37 Watan B-79, Inc. #6 | | | | | | | | |
| Starch fraction #1 | | | | | | | | 30.8 |
| Starch fraction #2 | | | | | | | | 12.0 |
| Starch fraction #3 | | | | | | | | 5.3 |
| Combined starches | | 71.5 | 7.8 | | | | | 47.2 |
| Bran protein | a | 27.4 | 7.0 | | | | | 30.7 |
| fraction | b | 18.8 | 8.6 | | | | | |
| Final mill water | a | 13 | 33 | | | | | 11.8 |
| | b | 11 | 9 | | | | | |
| Crude protein | | | 38.7 | | | | | 10.9 |
| Washed protein | | | 9.0 | 45.5 | 1.8 | 7.3 | 5.8 | 6.3 |
| Protein wash liquor | | | 85 | | | | | 4.5 |
| Syrup after protein centrifugation | | | | | | | | 35.0 |
| Celite-treated syrup | | | | | | | | 20.3 |
| R-38 Wanubet B-80, Inc. #BC | | | | | | | | |
| Starch fraction #1 | | | | | | | | 30.8 |
| Starch fraction #2 | | | | | | | | 12.0 |
| Starch fraction #3 | | | | | | | | 5.3 |
| Combined starches | | 78.0 | 3.4 | | | | | 47.2 |
| Bran protein | a | 30.9 | 9.6 | | | | | 30.7 |
| fraction | b | 34.2 | 9.3 | | | | | |
| Final mill water | a | 15.4 | 23.1 | | | | | 11.8 |
| | b | 11.8 | 31.4 | | | | | |
| Crude protein | | | 35.8 | | | | | 10.9 |
| Washed protein | | | 7.7 | 64.6 | 1.0 | 3.2 | 5.7 | 6.3 |
| Protein wash liquor | | | 85.7 | | | | | 4.5 |
| Syrup after protein centrifugation | | | | | | | | 35.0 |
| Celite-treated syrup | | | | | | | | 20.3 |
| R-39 Wanubet B-80, Inc. #BC | | | | | | | | |
| Starch fraction #1 | a | 67.9 | 3.2 | | | | | 30.1 |
| | b | 79.4 | 2.1 | | | | | |
| Starch fraction #2 | a | 64.4 | 2.1 | | | | | 11.7 |
| | b | 95.2 | 2.9 | | | | | |
| Starch fraction #3 | a | 83.2 | 3.2 | | | | | 7.4 |
| | b | 83.4 | 2.3 | | | | | |
| Combined starches | | 107.8 | 3.7 | | | | | 33.3 |
| Bran protein | a | 36.0 | 5.1 | | | | | 23.0 |
| fraction | b | 38.9 | 6.2 | | | | | |
| Final mill water | a | 18.9 | 20.8 | | | | | 13.4 |
| | b | 13.8 | 19.0 | | | | | |
| Crude protein | | | 57.4 | | | | | |
| Washed protein | | | 4.8 | 68.5 | 0.9 | 2.9 | 4.3 | 8.4 |
| Protein wash liquor | | | 86.7 | | | | | 3.3 |
| Syrup after protein centrifugation | | | | | | | | 31.5 |
| Celite-treated syrup | | | | | | | | 31.4 |
| R-40 Wanubet B-80, Inc. #BC | | | | | | | | |
| Starch fraction #1 | | | | | | | | 33.2 |
| Starch fraction #2 | | | | | | | | 12.9 |
| Starch fraction #3 | | | | | | | | 4.6 |
| Combined starches | | | | | | | | 54.3 |
| Bran protein | a | 27.2 | 8.9 | 15.6 | 3.2 | 7.5 | 1.4 | 19.1 |
| fraction | b | 30.7 | 7.4 | | | | | |
| Final mill water | a | 18.5 | 22.2 | | | | | 4.6 |
| | b | 13.5 | 32.7 | | | | | |
| Crude protein | | | 25.3 | | | | | 13.6 |
| Washed protein | | | 4.6 | 68.1 | 0.9 | 3.1 | 5.5 | 8.7 |
| Protein wash liquor | | | 84.2 | | | | | 3.9 |
| Syrup after protein centrifugation | | | | | | | | 39.5 |
| R-41 Wanutan B-79, Inc. #5 | | | | | | | | |
| Starch fraction #1 | | | | | | | | 41.6 |
| Starch fraction #2 | | | | | | | | 9.7 |
| Starch fraction #3 | | | | | | | | 5.1 |
| Combined starches | | 68.8 | 6.5 | | | | | 53.2 |
| Bran protein | | 18.3 | 7.3 | 14.8 | 4.6 | 15.2 | 1.3 | 18.7 |

-continued

| | % starch | % sol. sugar | % protein | % ash | % crude fiber | % Et$_2$O Ext. | Dry wt. 100 lbs barley |
|---|---|---|---|---|---|---|---|
| fraction | | | | | | | |
| Final mill water | 10.4 | 50.0 | | | | | 13.5 |
| Crude protein | | 24.1 | | | | | 16.3 |
| Washed protein | | 4.7 | 61.6 | 1.3 | 3.8 | 6.1 | 11.1 |
| Protein wash liquor | | 72.7 | | | | | 5.2 |
| Syrup after protein centrifugation | | | | | | | 41.3 |
| Celite-treated syrup | | | | | | | 33.2 |
| Carbon-treated syrup | | | | | | | 24.1 |

EXAMPLE VI

The following example illustrates the extraction of food grade proteins with ethyl alcohol.

Fifty pounds of hammermilled Washonupana B-79 was added to 200 pounds of water and treated with 0.1 units/g of Cereflo. After holding for 1 hour with gentle agitation the slurry was milled through the buhr mill, screened on the Rotex with an 80 mesh screen, and the material passing through the screen was centrifuged to remove the crude starch. The mill water (supernatant from the Bird centrifuge) was added back to the screen residue (bran protein) and the process repeated a second and third time as in all previous runs. The crude starch was then pasted at 75° C. for 10 minutes. Using 0.5% green malt as the liquefying enzyme, the mixture was cooled to 40° C. and 1% malt was added as a saccharifying agent. It was held at 40° C. for 2 hours, then heated to 60° C. and held for 1 hour. At this point the converted material was centrifuged as usual with the Bird centrifuge to separate the protein from the syrup. The protlein was washed twice with water to remove the sugar solution adhering to it. This is accomplished by resuspending the protein in water and running the slurry back through the Bird centrifuge. The protein was then extracted three times with absolute ethyl alcohol. The 85% alcohol is the most efficient concentration to remove fat and oil from starch. However, the protein was still wet, about 40% solids, so the first extraction removed the water present in the protein. The first extraction was for 30 minutes followed by a separation of the solids on the Bird; the second and third extractions were overnight extractions because it was convenient. These extractions could also be 30-60 minute extractions as well.

The yield of defatted protein was 5.9 pounds per 100 pounds of barley. It was apparent that the last alcohol extraction removed some of the protein present thus, reducing total yield. This could be modified depending on the type of equipment used.

The efficiency of this extraction of fat and oil from the barley protein is shown in the following example.

| Protein treatment | % sol sugars | % protein d.b. | % Et$_2$O ext. d.b. | % ash d.b. | % crude fiber d.b. |
|---|---|---|---|---|---|
| Crude protein | 24.2 | | | | |
| 1st water wash | 2.9 | | | | |
| 2nd water wash | 0.7 | 65.0 | 4.6 | | |
| 1st EtOH extraction | | 68.3 | 1.6 | | |

-continued

| Protein treatment | % sol sugars | % protein d.b. | % Et$_2$O ext. d.b. | % ash d.b. | % crude fiber d.b. |
|---|---|---|---|---|---|
| 2nd EtOH extraction | | 75.7 | 1.0 | | |
| 3rd EtOH extraction | | 71.6 | 0.1 | 0.9 | 5.3 |

By the third alcohol extraction the protein is almost free of water and therefore the alcohol is quite concentrated. It is apparent that this alcohol removed some nitrogen containing material, in all probability alcohol-soluble protein. By regulating the amount and concentration of the alcohol this loss could be eliminated. It is possible that by using a horizontal rotary vacuum filter the third extraction could be replaced by an alcohol wash on the filter. This would reduce the amount of alcohol required and could be adjusted to a result in minimum loss of protein.

The alcohol is recovered from the extracts by distillation, leaving the barley oil as a residue. The crude barley oil can be purified in the same manner as in corn oil. With this process, using both the crude protein separated from the syrup by the Bird and the additional crude protein separated from the treatment of the mill water with the Westfalia centrifuge, one can recover approximately ¾ of the oil present in the original barley, which amounts to 1.7 pounds per 100 pounds of barley using available varieties.

EXAMPLE VII

The following pilot plant run shows the result of recycling mill water. It will be noted that on recycle 1, 2, 3 there was obtained 0.7, 1.4 and 1.5 pounds of dry matter respectively (Westfalia solid). This was on 50 pounds of barley. The analytical data on these three samples is given below:

| Experiment | % fat | % protein | lbs/cwt barley | Yield of fat lbs/100 lbs barley |
|---|---|---|---|---|
| 1st cycle | 18.5 | 62.7 | 1.3 | 0.2 |
| 2nd cycle | 15.2 | 56.0 | 2.8 | 0.4 |
| 3rd cycle | 15.0 | 55.0 | 3.1 | 0.5 |
| PP#53 1 cycle | 11.5 | 60.0 | 1.7 | 0.3 |

In each case the pasteurized mill water was centrifuged and used in the makeup water for a fresh lot of ground barley.

The following shows the analysis of various products and streams from the same pilot plant run.

| Sample* | % solids | % soluble sugar a.i. | % soluble sugar d.b. | % starch d.b. | Solids yield dry weight |
|---|---|---|---|---|---|
| Bran Protein, 1st run | 19.7 | | 7.7 | 25 | 10.6 lb |
| Bran Protein, 2nd run | 20.7 | | 10.0 | 24 | 13.7 |
| Bran Protein, 3rd run | 20.6 | | 14.0 | 21 | 13.6 |
| Crude Starch, 1st run | has appreciable change | | 3.5 | 60 | 27.8 |
| Crude Starch, 2nd run | in amounts sugars build | | 4.1 | 79 | 23.8 |
| Crude Starch, 3rd run | up as expected little more starch in mill water probably small granule build up | | 6.2 | 65 | 26.0 |
| Westfalia Solids, 1st run | 30.2 | | | 3.0** | 0.7*** |
| Westfalia Solids, 2nd run | 27.4 | | | 5.1** | 1.4*** |
| Westfalia Solids 3rd run | 26.6 | | | 8.3** | 1.5*** |
| Westfalia Solids after dialysis | | | | | |
| Mill water, 1st run before cent. | 3.9 | 1.7 | 44 | 5.6 | 3.0 |
| Mill water, 2nd run before cent. | 6.9 | 2.7 | 39 | 13 | 7.5 |
| Mill water, 3rd run before cent. | 8.5 | 3.2 | 38 | 13 | 9.2 |
| Mill water, 1st run after cent. | 3.6 | 2.7 | 75 | 0.9 | |
| Mill water, 2nd run after cent. | 6.5 | 3.8 | 58 | 0.6 | 7.5 |
| Mill water, 3rd run after cent. | 7.2 | 4.1 | 57 | 1.0 | |
| Mill water, 3rd run after dialysis | 3.3 | 2.4 | 73 | | | a.i. = as is
d.b. = dry basis
*from 50# barley
cent = centrifuged
**includes soluble sugars
***50 pounds of barley used in each case so total of 3.6 pounds of dry solids came from 150 pounds of ground barley

EXAMPLE VIII

The following experiment sets forth results and data on treatment of mill water obtained from Experiments R-14 and R-42 disclosed above.

R-14—Mill water was recycled 3×, with water added as needed for the second and third runs:

| Runs | % solids | % Soluble Sugar a.i. | % Soluble Sugar d.b. | % Fresh water in slurry |
|---|---|---|---|---|
| 1st run | 5.4 | 1.7 | 31 | 100 |
| 2nd run | 10.4 | 4.7 | 45 | 33 |
| 3rd run | 12.0 | 5.5 | 46 | 48 |

R-42—Mill water was recycled 3×, centrifuged through the Westfalia after each run, and water added as needed for the second and third runs:

| | Before cent. | After cent. | Before a.i. | Before d.b. | After a.i. | After d.b. | % Fresh Water in slurry |
|---|---|---|---|---|---|---|---|
| 1st run | 3.9 | | 1.7 | 44 | | 0.9 | 100 |
| 2nd run | 6.9 | 6.5 | 2.7 | 39 | 58 | 0.6 | 35 |
| 3rd run | 8.5 | 7.2 | 3.2 | 38 | 57 | 1.0 | 44 |

Assume bran protein was pressed out to 50% moisture instead of 80% and the extra mill water was reused:

| | % fresh water in slurry |
|---|---|
| 1st run | 100 |
| 2nd run | 25 |
| 3rd run | 32 |

The following Table XI sets forth analyses of bran protein obtained from a series of pilot plant runs and Table XII sets forth mill water and precipitate analyses from a portion of these runs.

TABLE XI

Analysis of Bran Protein

| PR No | % dry matter | % Protein | % Ash | % Et$_2$O Ext. | % Crude Fiber | % ND* Fiber | % AD** Fiber | % sol sugars | % Starch | Yield lbs/100 lbs barley |
|---|---|---|---|---|---|---|---|---|---|---|
| A | 99.2 | 16.4 | 3.2 | 2.5 | 7.3 | 27.8 | 8.6 | 7 | 30 | 19.6 |
| B | 97.3 | 16.3 | 2.9 | 2.7 | 5.8 | 25.9 | 6.5 | 6 | 34 | 19.1 |
| C | 99.3 | 16.3 | 3.5 | 2.8 | 7.4 | 29.3 | 7.7 | 10 | 29 | 16.0 |
| D | 98.6 | 16.6 | 3.4 | 3.6 | 8.5 | 33.1 | 8.9 | 9 | 30 | 14.8 |
| E | 97.7 | 16.4 | 3.0 | 3.1 | 7.6 | 28.5 | 7.4 | 7 | 31 | 22.4 |
| F | 98.2 | 16.5 | 3.2 | 2.8 | 7.5 | 28.9 | 9.3 | 7 | 31 | 18.3 |

TABLE XI-continued

Analysis of Bran Protein

| PR No | % dry matter | % Protein | % Ash | % Et₂O Ext. | % Crude Fiber | % ND* Fiber | % AD** Fiber | % sol sugars | % Starch | Yield lbs/100 lbs barley |
|---|---|---|---|---|---|---|---|---|---|---|
| Composite | 98.5 | 16.6 | 3.5 | 3.0 | 8.1 | 30.1 | 9.0 | 6 | 34 | |

*Neutral detergent fiber
**Acid detergent fiber
All values are on an "as is" basis.

TABLE XII

Mill Water and Precipitate Separated with the Westfalia Centrifuge

| | % DM* | % Protein | % Ash | % Et₂O Ext. | % Crude Fiber | % Sol sugars d.b. | % Starch d.b. |
|---|---|---|---|---|---|---|---|
| PRA Mill Water | 95.2 | 27.0 | 3.4 | | | | |
| PRC Mill Water | 96.4 | 10.3 | 8.9 | 0.1 | 0.0 | 71 | |
| PRA ppt | 97.9 | 46.8 | 1.0 | 19.4 | 0.1 | | |
| PRC ppt 1st pass | 99.6 | 58.6 | 4.0 | 17.6 | 0.1 | | 17 |
| PRC ppt 2nd pass | 99.8 | 61.4 | 3.3 | 17.2 | 0.1 | | 11 |

*dry matter

Analytical Methods

A. The protein content of the grain, bran protein and protein samples was determined by the Kjeldahl method (1) (conversion factor 6.25).

B. The protein content of the syrup samples was determined by the Ehresmann method (2).

C. Moisture of syrup samples was determined by the Oven-Filter Aid method (3). Moisture of other samples was determined by the standard AOAC method (1).

D. The free fat was determined by ether extraction (1).

E. The samples were ashed according to the usual procedure (1).

F. Crude fiber was determined by the usual method (1).

G. Soluble sugar was determined by the Phenol-Sulfuric Acid Colorimetric method (4). The starches and solid samples were extracted three times with water and the washings combined and diluted to a standard volume. The determination was carried out on a suitable aliquot.

H. Starch was determined by the method of Baur and Alexander (5) on samples washed free of sugar (see G above), modified by the determination of the glucose formed by the hydrolysis of the starch by the method of Banks and Greenwood (6).

I. The activity of the green malt was determined by incubating an extract with Linter starch and measuring the reducing sugars according to the method of Whelan (7).

J. The sugar composition of the barley syrup was determined by high-pressure liquid chromatography, using a BioRad Aminex HPX-87 carbohydrate column (300 mm×7.8 mm) protected by an Aminex Q 150-S microguard cartridge in a Waters Associates LC composed of a R-401 refractive index detector, an M-45 pump, a U6K injector and a Model 730 Data Module. The solvent was degassed Milli-Q deionized water. The temperature of the column was held at 85° C. and the R.I. detector at 45° C.

K. Dietary fiber was determined by the neutral detergent fiber method of Roth et al (11).

(1) Association of Official Analytical Chemists. Official Methods of Analysis (11th ed.) The Association: Washington, D.C. (1970).
(2) Ehresmann, B., Spectrophotometric Determination of protein Concentration in Cell Extracts Containing tRNA's and rRNA's, Anal. Biochem. 54 (1973) 454–463.
(3) Standard Analytical Methods of the Member Companies of the Corn Industries Research Foundation, Inc., Corn Industries Research Foundation, Inc. Washington, D.C. (1954).
(4) Whistler, Roy L. (ed.), in Methods in Carbohydrate Chemistry, Vol. 1, Academic Press, New York (1962) 388–389.
(5) Baur, M. C. and R. J. Alexander, Enzymatic Procedures for the Determination of Starch in Cereal Products, Cereal Chem. 56 (1979) 364–366.
(6) Banks, W. and C. T. Greenwood, The Characterization of Starch and its Components. Part 4. The Specific Estimation of Glucose using Glucose Oxidase. Die Stärke, 23 (1971) 222–228.
(7) Whelan, W. J., Hydrolysis with α-Amylase in Methods in Carbohydrate Chemistry, vol. IV, ed. by Roy L. Whistler, Academic Press, New York: 1964.
(8) Mongean, R. and R. Brassard, Determination of Neutral Detergent Fiber, Hemicellulose, Cellulose, and Lignin in Breads. Cereal Chem. 56 (1979) 437–441.
(9) Schock, Thomas J., Fatty Substances in Starch in Methods in Carbohydrate Chemistry, Vol. IV, ed.by Roy L. Whistler. Academic Press, New York, 1964, 56–61.
(10) Goering, K. J., L. L. Jackson and B. W. DeHaas, Effect of Some Nonstarch Components in Corn and Barley Starch Granules on the Viscosity of Heated Starch-Water Suspensions, Cereal Chem. 52 (1975) 493–499.
(11) Roth, N. J. L., G. H. Watts and C. W. Newman, Beta-glucanase as an Aid in Measuring Detergent Fiber in Barley Kernels, in press, submitted to Cereal Chem.

The invention has been described herein by reference to certain preferred embodiments. However, as obvious variations thereon will become apparent to those skilled in the art the invention is not to be considered as limited thereto.

What is claimed is:

1. A process for the production of a maltose syrup from starch-containing material obtained from waxy barley by conversion of components in the starch to form maltose, the steps of the process comprising:
   (a) forming a 25–40 weight percent mixture of a waxy barley starch-containing material in water,;
   (b) adding to said mixture a sufficient amount of an enzyme which contains at least an amylase to effect at least partial hydrolysis of the starch-containing material and form maltose and produce a resulting mixture containing these components;
   (c) heating the resulting mixture to a temperature in the range of about 60°–76° C. for a sufficient period for the starch to dissolve so that starch granules do not remain in the resulting solution;
   (d) cooling the resulting solution, adding an additional portion of an enzyme which contains at least an amylase and continuing contact for a sufficient time to effect additional starch conversion and form maltose and produce a resulting mixture of these components;

(e) heating the resulting mixture at a temperature of about 50° C. to 70° C. to substantially complete starch conversion; and (f) separating and recovering the solids comprising proteins and liquids comprising a maltose syrup.

2. A process according to claim 1 wherein the enzyme is a waxy barley green malt which has both amylase and beta-glucanase activity.

3. A process according to claim 2 wherein about 0.5 wt% of the enzyme is added in each of steps (b) and (d) and the resulting mixture in step (e) is heated at a temperature of about 75° to 76° C. until the starch dissolves.

4. A process according to claim 3 wherein in step (d), the solution is cooled to about 40° C., about 0.5 wt% of enzyme is added to the starch solution, the mixture is held at a temperature in the range of about 40° C. for about 1–4 hours and then the temperature is raised to about 60° C. in step (e) for about 1 hour.

5. A process according to claim 1, wherein starch-containing starting material is obtained from whole waxy barley.

6. A process according to claim 1 wherein conversion of the starch is completed within a time period of about 24 hours or less.

7. A process according to claim 6 wherein the conversion time period is about 2 to 3 hours to produce a medium conversion syrup.

8. A process according to claim 4 wherein after removal of the protein from the maltose solution, the resulting solution is further held at about 60° C. for 1 to 2 hours to allow additional time for the enzyme to work, the resulting mixture is subjected to supercentrifugation to separate beta-glucans formed, and a light syrup product is recovered.

9. A process according to claim 8 wherein the beta-glucans are then dried to form a carbohydrate gum.

10. A process according to claim 4 wherein the protein solids are washed with water, dispersed in an aqueous solution of lactic acid, lactic acid insolubles are removed, the pH is adjusted to 6.0–6.5 and precipitated protein solids are separated from the water phase and recovered.

11. A process according to claim 10 wherein the lactic acid insolubles comprise a protein containing gel which contains about 85% water and are freeze-dried to yield a product containing at least 60–70 wt% of protein.

12. A process according to claim 10 wherein the precipitated protein solids are freeze-dried to produce a gluten product containing at least about 80 wt% protein.

13. A process according to claim 4 wherein the syrup is decolorized and then subjected to concentration to produce a concentrated syrup containing at least 80% solids and comprising at least about 60% maltose.

14. A process for the production of beta-glucan protein products and maltose containing syrup products from waxy barley grain, waxy barley flour or mixtures thereof, the steps of the process comprising:

(a) providing a waxy barley grain, waxy barely flour, or mixtures thereof, and mixing with sufficient water to assist in conditioning and milling of the grain or flour or mixtures thereof, to form a slurry;

(b) adding to the slurry a beta-glucanase-containing enzyme to at least partially hydrolyze beta-glucans contained in the flour or grain or mixtures thereof and release the beta-glucans from solution;

(c) milling the resulting mixture to effect grinding and separating at least a portion of a mixture comprising beta-glucans, protein and bran and process liquids, and provide a starch slurry;

(d) adjusting the solids content of the starch slurry to about 25–40 wt% starch solids by removal of excess liquid and adding to said mixture a sufficient amount of an amylase containing enzyme to effect at least partial hydrolysis of the starch and form maltose and produce a resulting mixture containing these components;

(e) heating the resulting mixture to a temperature in the range of about 60° to 76° C. for a sufficient period for the starch to dissolve and so that starch granules do not remain in the resulting solution;

(f) cooling the resulting solution, adding a further portion of an amylase-containing enzyme, and agitating for a sufficient time to effect additional starch conversion and form maltose and produce a resulting mixture of these components;

(g) heating the resulting mixture at a temperature of about 50° C. to 70° C. to substantially complete starch conversion; and (h) separating and recovering protein solids and liquids comprising a maltose syrup.

15. A process according to claim 14 wherein the waxy barley contains at least about 92% amylopectin.

16. A process according to claim 15 wherein the waxy barley is a member selected from the group consisting of Washonupana, Washonutan, Washonubet, Wanupana, Wanutan, Wanubet, Wapana, Watan, Wabet, and Waxy Oderbrucker.

17. A process according to claim 14 wherein the waxy barley starting material is whole waxy barley.

18. A process according to claim 14 wherein the waxy barley starting material is waxy barley flour.

19. A process according to claim 14 wherein conversion is completed within a time period of about 2–3 hours to produce a medium conversion maltose syrup.

20. A process according to claim 18 wherein the waxy barley flour is obtained from waxy barley grain by cleaning and milling the grain to remove most of the bran and produce the flour.

21. A process according to claim 14 wherein about 0.5% by weight of enzyme, based on the weight of the flour or grain or mixtures thereof is added to the mixture in each of steps (b), (d) and (f).

22. A process according to claim 21 wherein the enzyme added in steps (b), (d) and (f) is a waxy barley green malt having both beta-glucanase and alpha- and beta-amylase activity.

23. A process according to claim 14 wherein in step (c), the bran and associated proteins including at least some of the beta-glucans are separated from the starch portion on a screen, and the starch portion is used in step (d).

24. A process according to claim 22 wherein the proteins and bran are washed and dried to produce a bran protein product containing 20–25 wt% of protein content.

25. A process according to claim 14 wherein in steps (b), (d) and (f), about 0.5 wt% of the enzyme is added to the starch slurry, the mixture from step (d) is heated in step (e) at a temperature of about 75° to 76° C. until the starch dissolves, an enzyme having both alpha-amylase and beta-amylase activity is added to the starch solution, the mixture of step (f) is held at a temperature in the range of about 40° C. for about 1–4 hours with agitation, and then the temperature in step (g) is raised to about 60° C. for about 1 hour.

26. A process according to claim 25 wherein the solution of maltose syrup is further held at a temperature of about 60° C. for 1 to 2 hours and then subjected to supercentrifugation to separate beta-glucan as a gel and produce a light syrup product.

27. A process according to claim 26 wherein the beta-glucans are then dried to form a carbohydrate gum.

28. A process according to claim 25 wherein the protein solids are washed with water, dispersed in an aqueous solution of lactic acid, lactic acid insolubles are removed, the pH is adjusted to 6.0–6.5 and precipitated protein solids are separated from the solution and recovered.

29. A process according to claim 28 wherein the lactic acid insolubles comprise a protein containing gel which contains about 85% water and are freeze-dried to yield a product containing at least 60–70 wt% of protein.

30. A process according to claim 28 wherein the precipitated protein solids are freeze-dried to produce a gluten product containing at least about 80 wt% protein.

31. A process according to claim 25 wherein the syrup is decolorized and then subjected to concentration to produce a concentrated syrup containing at least 80% solids and comprising at least about 60% maltose.

32. A process according to claim 14 wherein process liquids are removed from the mixture of beta-glucans, protein and bran of step (c) and combined with the excess liquid removed in step (d) to form a mill water product, the mill water product is pasteurized by heating to an elevated temperature, and then subjected to a solids separation to produce a protein solids formed by presence of enzyme in the process liquids and a fermentable mill water.

33. A process according to claim 32 wherein the protein solids recovered from the mill water are combined with protein solids from step (h), the combined protein solids mixture is extracted with an alcohol to remove unsaturated oils, and there are recovered the protein solids and a barley oil.

34. A process according to claim 33 wherein the protein is recovered by solids separation, the barley oil is recovered by distillation of the alcohol, and the alcohol is recycled.

35. A process according to claim 32 wherein a portion of fermentable mill water is recycled to step (a) for mixing with waxy barley.

36. A process according to claim 32 wherein at least a portion of the fermentable mill water is reacted with an enzyme to convert sugars contained therein to ethyl alcohol and recovering the ethyl alcohol.

37. A process for the production of protein products, maltose containing syrups, and a beta-glucan carbohydrate gum from a waxy barley grain, the steps of the process comprising:
(a) milling the waxy barley grain;
(b) mixing the milled waxy barley grain with about 3–5 parts of water per part of milled waxy barley grain to form a slurry;
(c) adding about 0.5 weight percent of a green malt enzyme to at least partially hydrolyze beta-glucans contained in the milled waxy barley grain and reduce viscosity and release beta-glucans;
(d) removing at least a portion of the released beta-glucan solids from the mixture to provide a starch slurry;
(e) adjusting the solids content of the starch slurry to about 35–40 weight percent starch solids by removal of excess mill water liquid and adding to said mixture about 0.5 weight percent of a green malt enzyme to effect at least partial hydrolysis of the starch so as to form maltose and produce a resulting mixture containing these components;
(f) heating the resulting mixture at a temperature of about 75°–76° C. range for a sufficient period for the starch to dissolve and produce a solution;
(g) cooling the solution to a temperature of about 40° C., adding about 0.5 weight percent of a green malt enzyme, and agitating the mixture for a sufficient time to effect additional starch conversion by forming maltose and producing a resulting mixture of these components;
(h) heating the resulting mixture at a temperature of about 50° C. to 70° C. to substantially complete the starch conversion;
(i) separating and recovering the solids comprising proteins from liquids comprising a maltose syrup;
(j) removing mill water liquids from the beta-glucan solids of step (d) and combining with the excess liquid of step (e) and pasteurizing said combined liquids by heating at an elevated temperature to form additional protein solids by reason of the enzyme contained in the mill water liquids;
(k) separating the protein solids from the mill water liquids and recycling at least a portion of the mill water liquids to step (b);
(l) combining the protein solids with the protein solids from step (i) and extracting with an alcohol to remove unsaturated vegetable oils from the protein solids, recovering the purified protein solids; and
(m) removing the alcohol extractant and recovering a barley oil.

* * * * *